United States Patent
Hossainy

(10) Patent No.: US 7,217,426 B1
(45) Date of Patent: *May 15, 2007

(54) COATINGS CONTAINING POLYCATIONIC PEPTIDES FOR CARDIOVASCULAR THERAPY

(75) Inventor: Syed F. A. Hossainy, Fremont, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 266 days.

This patent is subject to a terminal disclaimer.

(21) Appl. No.: 10/177,117

(22) Filed: Jun. 21, 2002

(51) Int. Cl.
*A61F 2/02* (2006.01)
*A61K 47/30* (2006.01)

(52) U.S. Cl. .................. 424/426; 514/772.3
(58) Field of Classification Search ............... 424/426, 424/423; 514/772.3
See application file for complete search history.

(56) References Cited

U.S. PATENT DOCUMENTS

| | | |
|---|---|---|
| 2,072,303 A | 3/1937 | Herrmann et al. |
| 2,386,454 A | 10/1945 | Frosch et al. |
| 2,968,649 A | 1/1961 | Pailthorp et al. |
| 3,051,677 A | 8/1962 | Rexford |
| 3,178,399 A | 4/1965 | Lo |
| 3,324,069 A | 6/1967 | Koblitz et al. |
| 3,773,737 A | 11/1973 | Goodman et al. |
| 3,779,805 A | 12/1973 | Alsberg |
| 3,835,175 A | 9/1974 | Carpino et al. ............ 260/463 |
| 3,849,514 A | 11/1974 | Gray, Jr. et al. |
| 3,856,827 A | 12/1974 | Cavitt |
| 4,076,929 A | 2/1978 | Dohany |
| 4,197,380 A | 4/1980 | Chao et al. |
| 4,226,243 A | 10/1980 | Shalaby et al. |
| 4,304,010 A | 12/1981 | Mano |
| 4,329,383 A | 5/1982 | Joh |
| 4,343,931 A | 8/1982 | Barrows |
| 4,346,710 A | 8/1982 | Thanawalla et al. |
| 4,353,960 A | 10/1982 | Endo et al. |
| 4,399,264 A | 8/1983 | Squire |
| 4,413,359 A | 11/1983 | Akiyama et al. |
| 4,423,183 A | 12/1983 | Close |
| 4,485,250 A | 11/1984 | Squire |
| 4,529,792 A | 7/1985 | Barrows |
| 4,530,569 A | 7/1985 | Squire |
| 4,564,013 A | 1/1986 | Lilenfeld et al. |
| 4,569,978 A | 2/1986 | Barber |
| 4,611,051 A | 9/1986 | Hayes et al. |
| 4,632,842 A | 12/1986 | Karwoski et al. |
| 4,636,346 A | 1/1987 | Gold et al. |
| 4,656,242 A | 4/1987 | Swan et al. |
| 4,718,907 A | 1/1988 | Karwoski et al. |
| 4,733,665 A | 3/1988 | Palmaz |
| 4,749,585 A | 6/1988 | Greco et al. |
| 4,754,009 A | 6/1988 | Squire |
| 4,770,939 A | 9/1988 | Sietsess et al. |
| 4,800,882 A | 1/1989 | Gianturco |
| 4,871,357 A | 10/1989 | Hsu et al. |
| 4,876,109 A | 10/1989 | Mayer et al. |
| 4,882,168 A | 11/1989 | Casey et al. |
| 4,886,062 A | 12/1989 | Wiktor |
| 4,897,457 A | 1/1990 | Nakamura et al. |
| 4,908,404 A | 3/1990 | Benedict et al. |
| 4,910,276 A | 3/1990 | Nakamura et al. |
| 4,917,309 A | 4/1990 | Zander et al. ............... 241/5 |
| 4,931,287 A | 6/1990 | Bae et al. |
| 4,935,477 A | 6/1990 | Squire |
| 4,941,870 A | 7/1990 | Okada et al. |
| 4,948,851 A | 8/1990 | Squire |
| 4,973,142 A | 11/1990 | Squire |
| 4,975,505 A | 12/1990 | Squire |
| 4,977,008 A | 12/1990 | Squire |
| 4,977,025 A | 12/1990 | Squire |
| 4,977,026 A | 12/1990 | Squire |
| 4,977,297 A | 12/1990 | Squire |
| 4,977,901 A | 12/1990 | Ofstead ................... 128/772 |
| 4,982,056 A | 1/1991 | Squire |
| 4,985,308 A | 1/1991 | Squire |
| 4,999,248 A | 3/1991 | Squire |
| 5,000,547 A | 3/1991 | Squire |
| 5,006,382 A | 4/1991 | Squire |
| 5,019,096 A | 5/1991 | Fox, Jr. et al. |
| 5,025,001 A | 6/1991 | Loscalzo et al. ............ 514/91 |
| 5,030,394 A | 7/1991 | Sietses et al. |
| 5,047,020 A | 9/1991 | Hsu |
| 5,051,114 A | 9/1991 | Nemser et al. |

(Continued)

FOREIGN PATENT DOCUMENTS

DE 42 24 401 1/1994

(Continued)

OTHER PUBLICATIONS

Definition of Arginiine, Hawley's Condensed Chemical Dictionary, 14th Edition, 2002.*

(Continued)

*Primary Examiner*—Carlos A. Azpuru
(74) *Attorney, Agent, or Firm*—Squire, Sanders & Dempsey L.L.P.

(57) ABSTRACT

Coatings for implantable medical devices and methods for fabricating the same are disclosed. The coatings include a region containing a polycationic peptide, such as, for example, the polycationic peptide known as R7.

22 Claims, No Drawings

U.S. PATENT DOCUMENTS

| | | |
|---|---|---|
| 5,051,978 A | 9/1991 | Mayer et al. |
| 5,053,048 A | 10/1991 | Pinchuk |
| 5,076,659 A | 12/1991 | Bekiarian et al. |
| 5,093,427 A | 3/1992 | Barber |
| 5,100,992 A | 3/1992 | Cohn et al. |
| 5,107,852 A | 4/1992 | Davidson et al. |
| 5,110,645 A | 5/1992 | Matsumoto et al. |
| 5,112,457 A | 5/1992 | Marchant .................... 204/165 |
| 5,133,742 A | 7/1992 | Pinchuk |
| 5,155,137 A | 10/1992 | Keefer et al. ................ 514/611 |
| 5,163,952 A | 11/1992 | Froix |
| 5,165,919 A | 11/1992 | Sasaki et al. |
| 5,176,972 A | 1/1993 | Bloom et al. |
| 5,185,408 A | 2/1993 | Tang et al. |
| 5,187,183 A | 2/1993 | Loscalzo et al. ............. 514/400 |
| 5,202,129 A | 4/1993 | Samejima et al. .......... 424/489 |
| 5,219,980 A | 6/1993 | Swidler |
| 5,246,451 A | 9/1993 | Trescony et al. |
| 5,258,020 A | 11/1993 | Froix |
| 5,272,012 A | 12/1993 | Opolski |
| 5,276,121 A | 1/1994 | Resnick |
| 5,292,516 A | 3/1994 | Viegas et al. |
| 5,296,283 A | 3/1994 | Froggatt |
| 5,298,260 A | 3/1994 | Viegas et al. |
| 5,300,295 A | 4/1994 | Viegas et al. |
| 5,302,385 A | 4/1994 | Khan et al. |
| 5,306,501 A | 4/1994 | Viegas et al. |
| 5,306,786 A | 4/1994 | Moens et al. |
| 5,308,685 A | 5/1994 | Froggatt |
| 5,310,838 A | 5/1994 | Hung et al. |
| 5,324,889 A | 6/1994 | Resnick |
| 5,326,839 A | 7/1994 | Resnick |
| 5,328,471 A | 7/1994 | Slepian ....................... 604/101 |
| 5,330,768 A | 7/1994 | Park et al. |
| 5,336,518 A | 8/1994 | Narayanan et al. |
| 5,338,608 A | 8/1994 | Resnick |
| 5,342,348 A | 8/1994 | Kaplan |
| 5,353,368 A | 10/1994 | Resnick |
| 5,354,910 A | 10/1994 | Hung et al. |
| 5,356,890 A | 10/1994 | Loscalzo et al. ............. 514/210 |
| 5,366,997 A | 11/1994 | Keefer et al. ................ 614/611 |
| 5,368,566 A | 11/1994 | Crocker |
| 5,380,299 A | 1/1995 | Fearnot et al. |
| 5,383,853 A | 1/1995 | Jung et al. |
| 5,383,928 A | 1/1995 | Scott et al. |
| 5,395,311 A | 3/1995 | Andrews |
| 5,403,341 A | 4/1995 | Solar |
| 5,405,919 A | 4/1995 | Keefer et al. ................ 525/377 |
| 5,408,020 A | 4/1995 | Hung et al. |
| 5,417,969 A | 5/1995 | Hsu et al. |
| 5,417,981 A | 5/1995 | Endo et al. |
| 5,424,077 A | 6/1995 | Lajoie ......................... 424/641 |
| 5,428,070 A | 6/1995 | Cooke et al. ................ 514/557 |
| 5,443,458 A | 8/1995 | Eury |
| 5,447,724 A | 9/1995 | Helmus et al. |
| 5,455,040 A | 10/1995 | Marchant .................... 424/426 |
| 5,462,990 A | 10/1995 | Hubbell et al. |
| 5,464,650 A | 11/1995 | Berg et al. ................... 427/2.3 |
| 5,482,720 A | 1/1996 | Murphy et al. ............. 424/489 |
| 5,485,496 A | 1/1996 | Lee et al. |
| 5,516,881 A | 5/1996 | Lee et al. |
| 5,536,723 A | 7/1996 | Loscalzo et al. ............ 514/247 |
| 5,543,099 A | 8/1996 | Zhang et al. ................ 264/115 |
| 5,545,208 A | 8/1996 | Wolff et al. |
| 5,560,463 A | 10/1996 | Link et al. |
| 5,562,734 A | 10/1996 | King |
| 5,569,463 A | 10/1996 | Helmus et al. |
| 5,575,818 A | 11/1996 | Pinchuk |
| 5,578,073 A | 11/1996 | Haimovich et al. ......... 623/1 |
| 5,584,877 A | 12/1996 | Miyake et al. .............. 623/1 |
| 5,591,224 A | 1/1997 | Schwartz et al. |
| 5,604,283 A | 2/1997 | Wada et al. |
| 5,605,696 A | 2/1997 | Eury et al. ................... 424/423 |
| 5,607,467 A | 3/1997 | Froix |
| 5,609,629 A | 3/1997 | Fearnot et al. |
| 5,610,241 A | 3/1997 | Lee et al. |
| 5,616,338 A | 4/1997 | Fox, Jr. et al. |
| 5,616,608 A | 4/1997 | Kinsella et al. |
| 5,624,411 A | 4/1997 | Tuch |
| 5,628,728 A | 5/1997 | Tachibana et al. |
| 5,628,730 A | 5/1997 | Shapland et al. |
| 5,632,771 A | 5/1997 | Boatman et al. |
| 5,632,776 A | 5/1997 | Kurumatani et al. |
| 5,632,840 A | 5/1997 | Campbell |
| 5,635,201 A | 6/1997 | Fabo |
| 5,639,441 A | 6/1997 | Sievers et al. ............... 424/9.3 |
| 5,644,020 A | 7/1997 | Timmermann et al. |
| 5,646,239 A * | 7/1997 | Constancis et al. ......... 528/373 |
| 5,649,977 A | 7/1997 | Campbell |
| 5,650,442 A | 7/1997 | Mitchell et al. ............. 514/611 |
| 5,658,995 A | 8/1997 | Kohn et al. |
| 5,667,767 A | 9/1997 | Greff et al. .............. 424/9.411 |
| 5,670,558 A | 9/1997 | Onishi et al. ................ 523/112 |
| 5,674,242 A | 10/1997 | Phan et al. |
| 5,679,400 A | 10/1997 | Tuch |
| 5,684,061 A | 11/1997 | Ohnishi et al. |
| 5,691,311 A | 11/1997 | Maraganore et al. |
| 5,697,967 A | 12/1997 | Dinh et al. |
| 5,700,286 A | 12/1997 | Tartaglia et al. ............. 623/1 |
| 5,702,754 A | 12/1997 | Zhong |
| 5,711,958 A | 1/1998 | Cohn et al. |
| 5,713,949 A | 2/1998 | Jayaraman |
| 5,716,981 A | 2/1998 | Hunter et al. ............... 514/449 |
| 5,721,131 A | 2/1998 | Rudolph et al. |
| 5,723,219 A | 3/1998 | Kolluri et al. |
| 5,735,897 A | 4/1998 | Buirge |
| 5,746,998 A | 5/1998 | Torchilin et al. |
| 5,750,234 A | 5/1998 | Johnson et al. |
| 5,758,205 A | 5/1998 | Hara et al. |
| 5,759,205 A | 6/1998 | Valentini ..................... 623/16 |
| 5,760,118 A | 6/1998 | Sinclair et al. |
| 5,776,184 A | 7/1998 | Tuch |
| 5,780,579 A * | 7/1998 | Soula et al. ................. 528/332 |
| 5,783,657 A | 7/1998 | Pavlin et al. |
| 5,788,979 A | 8/1998 | Alt et al. |
| 5,800,392 A | 9/1998 | Racchini |
| 5,804,318 A | 9/1998 | Pinchuk et al. |
| 5,820,917 A | 10/1998 | Tuch |
| 5,824,048 A | 10/1998 | Tuch |
| 5,824,049 A | 10/1998 | Ragheb et al. ................ 623/1 |
| 5,827,587 A | 10/1998 | Fukushi |
| 5,830,178 A | 11/1998 | Jones et al. ................... 604/49 |
| 5,837,008 A | 11/1998 | Berg et al. |
| 5,837,313 A | 11/1998 | Ding et al. ................. 427/2.21 |
| 5,849,859 A | 12/1998 | Acemoglu |
| 5,851,508 A | 12/1998 | Greff et al. .............. 424/9.411 |
| 5,852,058 A | 12/1998 | Cooke et al. ................ 514/564 |
| 5,854,376 A | 12/1998 | Higashi |
| 5,858,746 A | 1/1999 | Hubbell et al. ............. 435/177 |
| 5,858,990 A | 1/1999 | Walsh |
| 5,860,963 A | 1/1999 | Azam et al. |
| 5,861,168 A * | 1/1999 | Cooke et al. ................ 424/424 |
| 5,865,814 A | 2/1999 | Tuch ........................... 604/265 |
| 5,869,127 A | 2/1999 | Zhong |
| 5,873,904 A | 2/1999 | Ragheb et al. ................ 623/1 |
| 5,874,165 A | 2/1999 | Drumheller |
| 5,876,433 A | 3/1999 | Lunn |
| 5,877,224 A | 3/1999 | Brocchini et al. |
| 5,879,697 A | 3/1999 | Ding et al. |
| 5,879,713 A | 3/1999 | Roth et al. |
| 5,891,459 A | 4/1999 | Cooke et al. ................ 424/439 |
| 5,897,911 A | 4/1999 | Loeffler |
| 5,900,425 A | 5/1999 | Kanikanti et al. |
| 5,902,875 A | 5/1999 | Roby et al. |

| Patent | Date | Inventor(s) | Patent | Date | Inventor(s) |
|---|---|---|---|---|---|
| 5,905,168 A | 5/1999 | Dos Santos et al. | 6,240,616 B1 | 6/2001 | Yan |
| 5,910,564 A | 6/1999 | Gruning et al. | 6,242,041 B1 | 6/2001 | Katoot et al. |
| 5,911,704 A | 6/1999 | Humes | 6,245,753 B1 | 6/2001 | Byun et al. |
| 5,914,387 A | 6/1999 | Roby et al. | 6,245,760 B1 | 6/2001 | He et al. |
| 5,919,893 A | 7/1999 | Roby et al. | 6,248,129 B1 | 6/2001 | Froix |
| 5,921,933 A | 7/1999 | Sarkis et al. | 6,251,136 B1 | 6/2001 | Guruwaiya et al. |
| 5,922,393 A | 7/1999 | Jayaraman | 6,254,632 B1 | 7/2001 | Wu et al. |
| 5,925,720 A | 7/1999 | Kataoka et al. | 6,258,121 B1 | 7/2001 | Yang et al. |
| 5,928,279 A | 7/1999 | Shannon et al. | 6,258,371 B1 | 7/2001 | Koulik et al. |
| 5,932,299 A | 8/1999 | Katoot | 6,262,034 B1 | 7/2001 | Mathiowitz et al. |
| 5,945,115 A | 8/1999 | Dunn et al. | 6,270,788 B1 | 8/2001 | Koulik et al. |
| 5,945,452 A | 8/1999 | Cooke et al. ............... 514/564 | 6,273,913 B1 | 8/2001 | Wright et al. |
| 5,955,509 A | 9/1999 | Webber et al. | 6,277,449 B1 | 8/2001 | Kolluri et al. |
| 5,958,385 A | 9/1999 | Tondeur et al. | 6,283,947 B1 | 9/2001 | Mirzaee |
| 5,962,138 A | 10/1999 | Kolluri et al. | 6,283,949 B1 | 9/2001 | Roorda |
| 5,971,954 A | 10/1999 | Conway et al. ............... 604/96 | 6,284,305 B1 | 9/2001 | Ding et al. |
| 5,980,928 A | 11/1999 | Terry ......................... 424/427 | 6,287,628 B1 | 9/2001 | Hossainy et al. |
| 5,980,972 A | 11/1999 | Ding ......................... 427/2.24 | 6,299,604 B1 | 10/2001 | Ragheb et al. |
| 5,997,517 A | 12/1999 | Whitbourne | 6,306,166 B1 | 10/2001 | Barry et al. ............... 623/1.46 |
| 6,010,530 A | 1/2000 | Goicoechea | 6,306,176 B1 | 10/2001 | Whitbourne |
| 6,011,125 A | 1/2000 | Lohmeijer et al. | 6,306,993 B1 | 10/2001 | Rothbard et al. ........... 526/304 |
| 6,015,541 A | 1/2000 | Greff et al. ............... 424/1.25 | 6,331,313 B1 | 12/2001 | Wong et al. |
| 6,033,582 A | 3/2000 | Lee et al. | 6,335,029 B1 | 1/2002 | Kamath et al. |
| 6,033,724 A | 3/2000 | Molitor | 6,344,035 B1 | 2/2002 | Chudzik |
| 6,034,204 A | 3/2000 | Mohr et al. | 6,346,110 B2 | 2/2002 | Wu |
| 6,042,875 A | 3/2000 | Ding et al. ............... 427/2.24 | 6,358,556 B1 | 3/2002 | Ding et al. |
| 6,051,576 A | 4/2000 | Ashton et al. | 6,362,271 B1 | 3/2002 | Lin et al. |
| 6,051,648 A | 4/2000 | Rhee et al. ............... 525/54.1 | 6,379,381 B1 | 4/2002 | Hossainy et al. |
| 6,054,553 A | 4/2000 | Groth et al. | 6,387,379 B1 | 5/2002 | Goldberg et al. |
| 6,056,993 A | 5/2000 | Leidner et al. ............. 427/2.25 | 6,395,326 B1 | 5/2002 | Castro et al. |
| 6,060,451 A | 5/2000 | DiMaio et al. ............... 514/13 | 6,408,878 B2 | 6/2002 | Unger et al. |
| 6,060,518 A | 5/2000 | Kabanov et al. | 6,410,612 B1 | 6/2002 | Hatanaka |
| 6,060,534 A | 5/2000 | Ronan et al. | 6,419,692 B1 | 7/2002 | Yang et al. |
| 6,063,432 A | 5/2000 | Maxwell et al. ............. 426/656 | 6,451,373 B1 | 9/2002 | Hossainy et al. |
| 6,077,543 A | 6/2000 | Gordon et al. ............... 424/489 | 6,464,683 B1 | 10/2002 | Samuelson et al. |
| 6,080,488 A | 6/2000 | Hostettler et al. ....... 428/423.3 | 6,482,834 B2 | 11/2002 | Spada et al. |
| 6,090,134 A | 7/2000 | Tu et al. | 6,494,862 B1 | 12/2002 | Ray et al. |
| 6,095,134 A | 8/2000 | Sievers et al. ......... 128/200.14 | 6,503,538 B1 | 1/2003 | Chu et al. |
| 6,096,070 A | 8/2000 | Ragheb et al. ................. 623/1 | 6,503,556 B2 | 1/2003 | Harish et al. |
| 6,096,396 A | 8/2000 | Patton et al. | 6,503,954 B1 | 1/2003 | Bhat et al. |
| 6,096,798 A | 8/2000 | Luthra et al. | 6,506,437 B1 | 1/2003 | Harish et al. |
| 6,096,809 A | 8/2000 | Lorcks et al. | 6,524,347 B1 | 2/2003 | Myers et al. |
| 6,099,562 A | 8/2000 | Ding et al. ............... 623/1.46 | 6,527,801 B1 | 3/2003 | Dutta |
| 6,099,563 A | 8/2000 | Zhong | 6,527,863 B1 | 3/2003 | Pacetti et al. |
| 6,110,188 A | 8/2000 | Narciso, Jr. ................. 606/153 | 6,528,526 B1 | 3/2003 | Myers et al. |
| 6,110,483 A | 8/2000 | Whitbourne et al. | 6,530,950 B1 | 3/2003 | Alvarado et al. |
| 6,113,629 A | 9/2000 | Ken ......................... 623/1.1 | 6,530,951 B1 | 3/2003 | Bates et al. |
| 6,117,872 A | 9/2000 | Maxwell et al. ............. 514/249 | 6,540,776 B2 | 4/2003 | Sanders Millare et al. |
| 6,120,491 A | 9/2000 | Kohn et al. | 6,544,223 B1 | 4/2003 | Kokish |
| 6,120,536 A | 9/2000 | Ding et al. ............... 623/1.43 | 6,544,543 B1 | 4/2003 | Mandrusov et al. |
| 6,120,788 A | 9/2000 | Barrows | 6,544,582 B1 | 4/2003 | Yoe |
| 6,120,904 A | 9/2000 | Hostettler et al. ....... 428/423.3 | 6,545,097 B2 | 4/2003 | Pinchuk et al. |
| 6,121,027 A | 9/2000 | Clapper et al. ............. 435/180 | 6,551,708 B2 | 4/2003 | Tsuda et al. |
| 6,124,045 A | 9/2000 | Soda et al. | 6,555,157 B1 | 4/2003 | Hossainy |
| 6,129,761 A | 10/2000 | Hubbell ......................... 623/11 | 6,558,733 B1 | 5/2003 | Hossainy et al. |
| 6,136,333 A | 10/2000 | Cohn et al. | 6,565,659 B1 | 5/2003 | Pacetti et al. |
| 6,143,354 A | 11/2000 | Koulik et al. | 6,572,644 B1 | 6/2003 | Moein |
| 6,153,252 A | 11/2000 | Hossainy et al. ............. 427/2.3 | 6,585,755 B2 | 7/2003 | Jackson et al. |
| 6,159,978 A | 12/2000 | Myers et al. | 6,585,765 B1 | 7/2003 | Hossainy et al. |
| 6,165,212 A | 12/2000 | Dereume et al. ........... 623/1.13 | 6,585,926 B1 | 7/2003 | Mirzaee |
| 6,172,167 B1 | 1/2001 | Stapert et al. | 6,605,154 B1 | 8/2003 | Villareal |
| 6,177,523 B1 | 1/2001 | Reich et al. | 6,616,765 B1 | 9/2003 | Castro et al. |
| 6,179,817 B1 | 1/2001 | Zhong | 6,623,448 B2 | 9/2003 | Slater |
| 6,180,632 B1 | 1/2001 | Myers et al. | 6,625,486 B2 | 9/2003 | Lundkvist et al. |
| 6,183,783 B1 | 2/2001 | Benoit et al. ............... 424/497 | 6,645,135 B1 | 11/2003 | Bhat |
| 6,197,051 B1 | 3/2001 | Zhong | 6,645,195 B1 | 11/2003 | Bhat et al. |
| 6,203,551 B1 | 3/2001 | Wu | 6,656,216 B1 | 12/2003 | Hossainy et al. |
| 6,211,249 B1 | 4/2001 | Cohn et al. | 6,656,506 B1 | 12/2003 | Wu et al. |
| 6,214,901 B1 | 4/2001 | Chudzik et al. | 6,660,034 B1 | 12/2003 | Mandrusov et al. |
| 6,224,894 B1 | 5/2001 | Jamiolkowski et al. | 6,663,662 B2 | 12/2003 | Pacetti et al. |
| 6,228,346 B1 | 5/2001 | Zhang et al. ............... 424/45 | 6,663,880 B1 | 12/2003 | Roorda et al. |
| 6,231,590 B1 | 5/2001 | Slaikeu et al. | 6,666,880 B1 | 12/2003 | Chiu et al. |
| 6,231,600 B1 | 5/2001 | Zhong | 6,673,154 B1 | 1/2004 | Pacetti et al. |

| Patent Number | Date | Inventor |
|---|---|---|
| 6,673,385 B1 | 1/2004 | Ding et al. |
| 6,689,099 B2 | 2/2004 | Mirzaee |
| 6,695,920 B1 | 2/2004 | Pacetti et al. |
| 6,706,013 B1 | 3/2004 | Bhat et al. |
| 6,709,514 B1 | 3/2004 | Hossainy |
| 6,712,845 B2 | 3/2004 | Hossainy |
| 6,713,119 B2 | 3/2004 | Hossainy et al. |
| 6,716,444 B1 | 4/2004 | Castro et al. |
| 6,733,768 B2 | 5/2004 | Hossainy et al. |
| 6,740,040 B1 | 5/2004 | Mandrusov et al. |
| 6,743,462 B1 | 6/2004 | Pacetti |
| 6,746,481 B1 | 6/2004 | Larik et al. |
| 6,746,773 B2 | 6/2004 | Llanos et al. |
| 6,749,626 B1 | 6/2004 | Bhat et al. |
| 6,753,071 B1 | 6/2004 | Pacetti et al. |
| 6,758,859 B1 | 7/2004 | Dang et al. |
| 6,759,054 B2 | 7/2004 | Chen et al. |
| 6,764,505 B1 | 7/2004 | Hossainy et al. |
| 7,070,798 B1 * | 7/2006 | Michal et al. ............... 424/423 |
| 2001/0007083 A1 | 7/2001 | Roorda |
| 2001/0014717 A1 | 8/2001 | Hossainy et al. |
| 2001/0018469 A1 | 8/2001 | Chen et al. |
| 2001/0020011 A1 | 9/2001 | Mathiowitz et al. |
| 2001/0029351 A1 | 10/2001 | Falotico et al. |
| 2001/0037145 A1 | 11/2001 | Guruwaiya et al. |
| 2001/0051608 A1 | 12/2001 | Mathiowitz et al. |
| 2002/0005206 A1 | 1/2002 | Falotico et al. |
| 2002/0007213 A1 | 1/2002 | Falotico et al. |
| 2002/0007214 A1 | 1/2002 | Falotico |
| 2002/0007215 A1 | 1/2002 | Falotico et al. |
| 2002/0009604 A1 | 1/2002 | Zamora et al. |
| 2002/0016625 A1 | 2/2002 | Falotico et al. |
| 2002/0032414 A1 | 3/2002 | Ragheb et al. |
| 2002/0032434 A1 | 3/2002 | Chudzik et al. |
| 2002/0051730 A1 | 5/2002 | Bodnar et al. |
| 2002/0071822 A1 | 6/2002 | Uhrich |
| 2002/0077693 A1 | 6/2002 | Barclay et al. |
| 2002/0082679 A1 | 6/2002 | Sirhan et al. |
| 2002/0087123 A1 | 7/2002 | Hossainy et al. |
| 2002/0090389 A1 | 7/2002 | Humes et al. |
| 2002/0091433 A1 | 7/2002 | Ding et al. |
| 2002/0094440 A1 | 7/2002 | Llanos et al. ............... 428/421 |
| 2002/0099438 A1 | 7/2002 | Furst |
| 2002/0111590 A1 | 8/2002 | Davila et al. ............... 604/265 |
| 2002/0120326 A1 | 8/2002 | Michal |
| 2002/0122877 A1 | 9/2002 | Harish et al. |
| 2002/0123801 A1 | 9/2002 | Pacetti et al. |
| 2002/0133183 A1 | 9/2002 | Lentz et al. |
| 2002/0142039 A1 | 10/2002 | Claude |
| 2002/0143386 A1 | 10/2002 | Davila et al. |
| 2002/0155212 A1 | 10/2002 | Hossainy |
| 2002/0165608 A1 | 11/2002 | Llanos et al. |
| 2002/0176849 A1 | 11/2002 | Slepian |
| 2002/0183581 A1 | 12/2002 | Yoe et al. |
| 2002/0188037 A1 | 12/2002 | Chudzik et al. |
| 2002/0188277 A1 | 12/2002 | Roorda et al. |
| 2003/0004141 A1 | 1/2003 | Brown |
| 2003/0004563 A1 | 1/2003 | Jackson et al. |
| 2003/0028243 A1 | 2/2003 | Bates et al. |
| 2003/0028244 A1 | 2/2003 | Bates et al. |
| 2003/0031780 A1 | 2/2003 | Chudzik et al. |
| 2003/0032767 A1 | 2/2003 | Tada et al. |
| 2003/0036794 A1 | 2/2003 | Ragheb et al. |
| 2003/0039689 A1 | 2/2003 | Chen et al. |
| 2003/0040712 A1 | 2/2003 | Ray et al. |
| 2003/0040790 A1 | 2/2003 | Furst |
| 2003/0059520 A1 | 3/2003 | Chen et al. |
| 2003/0060877 A1 | 3/2003 | Falotico et al. |
| 2003/0065346 A1 | 4/2003 | Evens et al. |
| 2003/0065377 A1 | 4/2003 | Davila et al. |
| 2003/0072868 A1 | 4/2003 | Harish et al. |
| 2003/0073961 A1 | 4/2003 | Happ |
| 2003/0077312 A1 | 4/2003 | Schmulewicz et al. |
| 2003/0083646 A1 | 5/2003 | Sirhan et al. |
| 2003/0083739 A1 | 5/2003 | Cafferata |
| 2003/0097088 A1 | 5/2003 | Pacetti |
| 2003/0097173 A1 | 5/2003 | Dutta |
| 2003/0099712 A1 | 5/2003 | Jayaraman |
| 2003/0105518 A1 | 6/2003 | Dutta |
| 2003/0113439 A1 | 6/2003 | Pacetti et al. |
| 2003/0150380 A1 | 8/2003 | Yoe |
| 2003/0157241 A1 | 8/2003 | Hossainy et al. |
| 2003/0158517 A1 | 8/2003 | Kokish |
| 2003/0190406 A1 | 10/2003 | Hossainy et al. |
| 2003/0207020 A1 | 11/2003 | Villareal |
| 2003/0211230 A1 | 11/2003 | Pacetti et al. |
| 2004/0018296 A1 | 1/2004 | Castro et al. |
| 2004/0029952 A1 | 2/2004 | Chen et al. |
| 2004/0047978 A1 | 3/2004 | Hossainy et al. |
| 2004/0047980 A1 | 3/2004 | Pacetti et al. |
| 2004/0052858 A1 | 3/2004 | Wu et al. |
| 2004/0052859 A1 | 3/2004 | Wu et al. |
| 2004/0054104 A1 | 3/2004 | Pacetti |
| 2004/0060508 A1 | 4/2004 | Pacetti et al. |
| 2004/0062853 A1 | 4/2004 | Pacetti et al. |
| 2004/0063805 A1 | 4/2004 | Pacetti et al. |
| 2004/0071861 A1 | 4/2004 | Mandrusov et al. |
| 2004/0072922 A1 | 4/2004 | Hossainy et al. |
| 2004/0073298 A1 | 4/2004 | Hossainy |
| 2004/0086542 A1 | 5/2004 | Hossainy et al. |
| 2004/0086550 A1 | 5/2004 | Roorda et al. |
| 2004/0096504 A1 | 5/2004 | Michal |
| 2004/0098117 A1 | 5/2004 | Hossainy et al. |
| 2004/0102758 A1 | 5/2004 | Davila et al. |

FOREIGN PATENT DOCUMENTS

| | | |
|---|---|---|
| DE | 19723723 | 12/1998 |
| EP | 0 301 856 | 2/1989 |
| EP | 0 396 429 | 11/1990 |
| EP | 0 514 406 | 11/1992 |
| EP | 0568310 | 11/1993 |
| EP | 0 604 022 | 6/1994 |
| EP | 0 623 354 | 11/1994 |
| EP | 0633032 | 1/1995 |
| EP | 0 665 023 | 8/1995 |
| EP | 0 677 332 A2 | 10/1995 |
| EP | 0 701 802 | 3/1996 |
| EP | 0 716 836 | 6/1996 |
| EP | 0747069 | 12/1996 |
| EP | 0 809 999 | 12/1997 |
| EP | 0 815 803 | 1/1998 |
| EP | 0 832 655 | 4/1998 |
| EP | 0 850 651 | 7/1998 |
| EP | 0 879 595 | 11/1998 |
| EP | 0 893 108 | 1/1999 |
| EP | 0 910 584 | 4/1999 |
| EP | 0 923 953 | 6/1999 |
| EP | 0 950 385 | 10/1999 |
| EP | 0 950 386 | 10/1999 |
| EP | 0 953 320 | 11/1999 |
| EP | 0 968 688 | 1/2000 |
| EP | 0 970 711 | 1/2000 |
| EP | 0 982 041 | 3/2000 |
| EP | 0 997 115 | 5/2000 |
| EP | 1 023 879 | 8/2000 |
| EP | 1 192 957 | 4/2002 |
| EP | 1 273 314 | 1/2003 |
| JP | 2001-190687 | 7/2001 |
| SU | 872531 | 10/1981 |
| SU | 876663 | 10/1981 |
| SU | 905228 | 2/1982 |
| SU | 790725 | 2/1983 |
| SU | 1016314 | 5/1983 |
| SU | 811750 | 9/1983 |
| SU | 1293518 | 2/1987 |

| | | |
|---|---|---|
| WO | WO 91/12846 | 9/1991 |
| WO | WO 92/05695 | 4/1992 |
| WO | WO 92/18320 | 10/1992 |
| WO | WO 94/02185 | 2/1994 |
| WO | WO 94/09760 | 5/1994 |
| WO | WO 94/28721 | 12/1994 |
| WO | WO 95/10989 | 4/1995 |
| WO | WO 95/24929 | 9/1995 |
| WO | WO 96/21404 | 7/1996 |
| WO | WO 96/40174 | 12/1996 |
| WO | WO 97/10011 | 3/1997 |
| WO | WO 97/16983 | 5/1997 |
| WO | WO 97/41164 | 11/1997 |
| WO | WO 97/45105 | 12/1997 |
| WO | WO 97/46590 | 12/1997 |
| WO | WO 98/06389 | 2/1998 |
| WO | WO 98/08463 | 3/1998 |
| WO | WO 98/13405 | 4/1998 |
| WO | WO 98/17331 | 4/1998 |
| WO | WO 98/32398 | 7/1998 |
| WO | WO 98/36784 | 8/1998 |
| WO | WO 98/49199 | 11/1998 |
| WO | WO 98/58680 | 12/1998 |
| WO | WO 99/00070 | 1/1999 |
| WO | WO 99/01118 | 1/1999 |
| WO | WO 99/32051 | 7/1999 |
| WO | WO 99/38546 | 8/1999 |
| WO | WO 99/55396 | 11/1999 |
| WO | WO 99/59433 | 11/1999 |
| WO | WO 99/63981 | 12/1999 |
| WO | WO 99/66921 | 12/1999 |
| WO | WO 00/02599 | 1/2000 |
| WO | WO 00/12147 | 3/2000 |
| WO | WO 00/18446 | 4/2000 |
| WO | WO 00/27455 | 5/2000 |
| WO | WO 00/29043 | 5/2000 |
| WO | WO 00/32255 | 6/2000 |
| WO | WO 00/38754 | 7/2000 |
| WO | WO 00/41738 | 7/2000 |
| WO | WO 00/46395 | 8/2000 |
| WO | WO 00/64506 | 11/2000 |
| WO | WO 00/74701 | 12/2000 |
| WO | WO 01/01890 | 1/2001 |
| WO | WO 01/08684 | 2/2001 |
| WO | WO 01/13957 | 3/2001 |
| WO | WO 01/15751 | 3/2001 |
| WO | WO 01/17577 | 3/2001 |
| WO | WO 01/30403 | 5/2001 |
| WO | WO 01/45763 | 6/2001 |
| WO | WO 01/49338 | 7/2001 |
| WO | WO 01/49340 | 7/2001 |
| WO | WO 01/51027 | 7/2001 |
| WO | WO 01/62297 | 8/2001 |
| WO | WO 01/74414 | 10/2001 |
| WO | WO 01/87342 | 11/2001 |
| WO | WO 01/87368 | 11/2001 |
| WO | WO 01/87372 | 11/2001 |
| WO | WO 01/87376 | 11/2001 |
| WO | WO 02/03890 | 1/2002 |
| WO | WO 02/24249 | 3/2002 |
| WO | WO 02/26139 | 4/2002 |
| WO | WO 02/26162 | 4/2002 |
| WO | WO 02/26271 | 4/2002 |
| WO | WO 02/26281 | 4/2002 |
| WO | WO 02/34311 | 5/2002 |
| WO | WO 02/47731 | 6/2002 |
| WO | WO 02/47732 | 6/2002 |
| WO | WO 02/056790 | 7/2002 |
| WO | WO 02/058753 | 8/2002 |
| WO | WO 02/102283 | 12/2002 |
| WO | WO 03/000308 | 1/2003 |
| WO | WO 03/022323 | 3/2003 |
| WO | WO 03/022324 | 3/2003 |
| WO | WO 03/028780 | 4/2003 |
| WO | WO 03/037223 | 5/2003 |
| WO | WO 03/039612 | 5/2003 |
| WO | WO 03/080147 | 10/2003 |
| WO | WO 03/082368 | 10/2003 |
| WO | WO 04/000383 | 12/2003 |
| WO | WO 04/009145 | 1/2004 |

OTHER PUBLICATIONS

U.S. Appl. No. 10/176,499, filed Jun. 21, 2002, Hossainy et al.
U.S. Appl. No. 10/176,504, filed Jun. 21, 2002, Roorda et al.
U.S. Appl. No. 10/176,506, filed Jun. 21, 2002, Claude et al.
U.S. Appl. No. 10/176,510, filed Jun. 21, 2002, Hossainy et al.
U.S. Appl. No. 10/177,114, filed Jun. 21, 2002, Simhambhatla et al.
U.S. Appl. No. 10/177,116, filed Jun. 21, 2002, Pacetti et al.
U.S. Appl. No. 10/177,154, filed Jun. 21, 2002, Hossainy et al.
U.S. Appl. No. 10/177,156, filed Jun. 21, 2002, Michal et al.
U.S. Appl. No. 10/177,942, filed Jun. 21, 2002, Michal et al.
U.S. Appl. No. 10/198,912, filed Jul. 19, 2002, Ding et al.
U.S. Appl. No. 10/320,899, filed Dec. 16, 2002, Shah et al.
U.S. Appl. No. 10/376,348, filed Feb. 26, 2003, Ding et al.
U.S. Appl. No. 10/428,691, filed May 1, 2003, Pacetti.
U.S. Appl. No. 10/931,927, filed Aug. 31, 2004, Pacetti.
Anonymous, Reducing the pH of a peptide oligomer to prepare for systemic delivery, Defensive Publication, Research Disclosure, p. 905 (Aug. 2003).
Anonymous, *Cardiologists Draw—Up The Dream Stent*, Clinica 710:15 (Jun. 17, 1996), http://www.dialogweb.com/cgi/document?req=1061848202959, printed Aug. 25, 2003 (2 pages).
Anonymous, *Heparin-coated stents cut complications by 30%*, Clinica 732:17 (Nov. 18, 1996), http://www.dialogweb.com/cgi/document?req=1061847871753, printed Aug. 25, 2003 (2 pages).
Anonymous, *Rolling Therapeutic Agent Loading Device for Therapeutic Agent Delivery or Coated Stent* (Abstract 434009), Res. Disclos. pp. 974-975 (Jun. 2000).
Anonymous, *Stenting continues to dominate cardiology*, Clinica 720:22 (Sep. 2, 1996), http://www.dialogweb.com/cgi/document?req=1061848017752, printed Aug. 25, 2003 (2 pages).
Aoyagi et al., *Preparation of cross-linked aliphatic polyester and application to thermo-responsive material*, Journal of Controlled Release 32:87-96 (1994).
Arnold et al., *Effects of environment on the creep properties of a poly (ethylmethacrylate) based bone cement* J. Mater. Sci: Mater. In Med., vol. 12, pp. 707-717 (2001).
Barath et al., *Low Dose of Antitumor Agents Prevents Smooth Muscle Cell Proliferation After Endothelial Injury*, JACC 13(2): 252A (Abstract) (Feb. 1989).
Barbucci et al., *Coating of commercially available materials with a new heparinizable material*, J. Biomed. Mater. Res. 25: 1259-1274 (Oct. 1991).
Bellex International, CYTOP®, *Amorphous Fluorocarbon Polymer*, 1 page, no date.
Bellex International, *Selected CYTOP Physical Data*, 1 page, no date.
Bellex International, *CYTOP* ®, http://www.bellexinternational.com/cytop.htm, printed Mar. 30, 2001, 1 page.
Chung et al., *Inner core segment design for drug delivery control of thermo-responsive polymeric micelles*, Journal of Controlled Release 65:93-103 (2000).
Cifková et al., *Irritation effects of residual products derived from p(HEMA) gels*, Biomaterials, vol. 9, (Jul. 1998), pp. 372-375.
Dalsin et al., *DOPA: A New Anchor for PEGylation of Biomaterial Surfaces*, Soc. For Biomaterials 28th Annual Meeting Transactions, pp. 40 (2002).
Deb et al., *Effect of crosslinking agents on poly(ethylmethacrylate) bone cements*, J. of Mater.Sci: Mater. In Med., vol. 8, pp. 829-833 (1997).
Del Guerra et al., *In vitro biocompatibility of fluorinated polyurethanes*, J. Mater. Sci. in Med., vol. 5, pp. 452-456 (1994).

Dev et al., *Kinetics of Drug Delivery to the Arterial Wall Via Polyurethane-Coated Removable Nitinol Stent: Comparative Study of Two Drugs*, Catheterization and Cardiovascular Diagnosis 34:272-278 (1995).

Dichek et al., *Seeding of Intravascular Stents with Genetically Engineered Endothelial Cells*, Circ. 80(5):1347-1353 (Nov. 1989).

DuPont, *Teflon AF 1601S amorphous fluoropolymer solutions*, product information, 2 pages (1998).

DuPont, *Processing of Teflon® AF*, Teflon Amorphous Fluoropolymer, http://www.dupont.com/teflon/af/processing.html, printed Mar. 30, 2001, 1 page.

DuPont, *High-Performance/Potential Applications*, Teflon Amorphous Fluoropolymer, http://www.dupont.com/teflon/af/potapps.html, printed Mar. 30, 2001, 3 pages.

DuPont, *Performance Comparison of Teflon AF*, Teflon Amorphous Fluoropolymer, http://www.dupont.com/teflon/af/performance.html, printed Mar. 30, 2001, 3 pages.

DuPont, *Unique Properties of Teflon® AF*, Teflon Amorphous Fluoropolymer, http://www.dupont.com/teflon/af/unique.html, printed Mar. 30, 2001, 3 pages.

DuPont, *Teflon® AF: A New Generation of High-Performance Fluoropolymer Resins*, http://www.dupont.com/teflon/af/index.html, printed Mar. 30, 2001, 1 page.

DuPont, *Teflon® Protects Superconductors Against Acid*, Teflon Amorphous Fluoropolymer, http://www.dupont.com/teflon/af/superconductor.html, printed Sep. 21, 2004, 2 pages.

DuPont, *Available Grades of Dupont Teflon® AF*, Teflon Amorphous Fluoropolymer, http://www.dupont.com/teflon/af/grades.html, printed Sep. 21, 2004, 2 pages.

DuPont, *Teflon® AF amorphous fluoropolymers*, Product Information, 6 pages (1998).

DuPont, Sales Notice, *Teflon Amorphous Fluoropolymer*, http://www.dupont.com/teflon/af/patent.html, printed Sep. 21, 2004, 2 pages.

Eigler et al., *Local Arterial Wall Drug Delivery from a Polymer Coated Removable Metallic Stent: Kinetics, Distribution, and Bioactivity of Forskolin*, JACC, 4A (701-1), Abstract (Feb. 1994).

Fine et al., *Improved nerve regeneration through piezoelectric vinylidenefluoride-trifluoroethylene copolymer guidance channels*, Biomaterials, vol. 12, Oct., pp. 775-780 (1991).

Fischell, *Polymer Coatings for Stents*, Circulation, 94:1494-95 (1996).

Gullickson, *Reference Data Sheet on Common Chlorinated Solvents*, http://www.mcs.net/~hutter/tee/chlorina.html, printed Mar. 30, 2001, 5 pages.

Gunn et al., *Stent coatings and local drug delivery*, Eur. Heart J., vol. 20, issue 23, pp. 1693-1700 (1999).

Harper et al., *Fatigue Characteristics of Polyethylmethacrylate Based Bone Cement Reinforced with Silane Coupled Hydroxyapatite*, Fifth World Biomaterials Congress, May 29-Jun. 2, 1996, Toronto, Canada, Abstract 351, 3 pgs.

Harper et al., *Mechanical properties of hydroxyapatite reinforced poly (ethyl methacrylate) bone cement after immersion in a physiological solution: influence of a silane coupling agent*, J. Mater. Sci.: Mater. In Med., vol. 11, pp. 491-497 (2000).

Helmus, *Overview of Biomedical Materials*, MRS Bulletin, pp. 33-38 (Sep. 1991).

Herdeg et al., *Antiproliferative Stent Coatings: Taxol and Related Compounds*, Semin. Intervent. Cardiol. 3:197-199 (1998).

Huang et al., *Biodegradable Polymers Derived from Aminoacids*, Macromol. Symp. 144, 7-32 (1999).

Inoue et al., *An AB block copolymer of oligo(methyl methacrylate) and poly(acrylic acid) for micellar delivery of hydrophobic drugs*, Journal of Controlled Release 51:221-229 (1998).

Kataoka et al., *Block copolymer micelles as vehicles for drug delivery*, Journal of Controlled Release 24:119-132 (1993).

Katsarava et al., *Amino Acid-Based Bioanalogous Polymers. Synthesis and Study of Regular Poly(ester amide)s Based on Bis(α-amino acid)α,ω-Alkylene Diesters, and Aliphatic Dicarbolic Acids*, Journal of Polymer Science, Part A: Polymer Chemistry, 37(4), 391-407 (1999).

Kruft et al., *Studies on radio-opaque polymeric biomaterials with potential applications to endovascular prostheses*, Biomaterials, vol. 17, No. 18, pp. 1803-1812 (1996).

Lambert et al., *Localized Arterial Wall Drug Delivery From a Polymer-Coated Removable Metallic Stent*, Circulation, vol. 90, No. 2, pp. 1003-1011 (1994).

Laroche et al., *Polyvinylidene fluoride (PVDF) as a biomaterial: From polymeric raw material to monofilament vascular suture*, J. of Biomedical Mat. Research, vol. 29, pp. 1525-1536 (1995).

Levy et al., *Strategies For Treating Arterial Restenosis Using Polymeric Controlled Release Implants*, Biotechnol. Bioact. Polym. [Proc. Am. Chem. Soc. Symp.], pp. 259-268 (1994).

Lin et al., *Fluropolymer Alloys Performance Optimization of PVDF Alloys*, Fluropolymers 2 Properties, edited by Hougham et al., Plenum Publishers N.Y. pp. 121-136 (1999).

Lin et al., *Surface characterization and platelet adhesion studies on fluorocarbons prepared by plasma-induced graft polymerization*, J. Biomater Sci. Polymer Edn., vol. 11, No. 7, pp. 701-714 (2000).

Liu et al., *Drug release characteristics of unimolecular polymeric micelles*, Journal of Controlled Release 68:167-174 (2000).

Luthra, Biointeractions Ltd (BIL), http://www.biomateria.com/biointeractions.html, printed Sep. 21, 2004, 3 pages.

3M, *Specialty Fluids 3M™ Fluorinert™ Liquids, Typical Properties*, http://www.3m.com/market/industrial/fluids/fluoprop.html, printed Mar. 30, 2001, 3 pages.

Materials Engineering, *Applications in Design/Manufacturing/R&D*, Materials Selector 1993, Penton Publishing (1992) 6 pgs.

Marconi et al., *Covalent bonding of heparin to a vinyl copolymer for biomedical applications*, Biomaterials 18(12):885-890 (1997).

Matsumaru et al., *Embolic Materials For Endovascular Treatment of Cerebral Lesions*, J. Biomater. Sci. Polymer Edn 8(7):555-569 (1997).

Medtronic, Trillium Affinity NT, Oxygenator, Product Information, 6 pages (2000).

Miyazaki et al., *Antitumor Effect of Implanted Ethylene-Vinyl Alcohol Copolymer Matrices Containing Anticancer Agents on Ehrlich Ascites Carcinoma and P388 Leukemia in Mice*, Chem. Pharm. Bull. 33(6) 2490-2498 (1985).

Miyazawa et al., *Effects of Pemirolast and Tranilast on Intimal Thickening After Arterial Injury in the Rat*, J. Cardiovasc. Pharmacol., pp. 157-162 (1997).

NCMS SOLV-DB, *Query Results for: CFC*, http://solvdb.ncms.org/CAT01.idc?chemcat=CFC, printed Mar. 30, 2001, 2 pages.

NCMS SOLV-DB, *Query Results for: FC-75 Fluorinert*, http://solvdb.ncms.org/common01.idc, printed Mar. 30, 2001, 2 pages.

Nordrehaug et al., *A novel biocompatible coating applied to coronary stents*, European Heart Journal 14, p. 321 (P1694), Abstr. Suppl. (1993).

Novick et al., *Protein-containing hydrophobic coatings and films*, Biomaterials, vol. 23, No. 2 (2002) pp. 441-448.

Ohsawa et al., *Preventive Effects of an Antiallergic Drug, Pemirolast Potassium, on Restenosis After Percutaneous Transluminal Coronary Angioplasty*, American Heart Journal 136(6):1081-1087 (Dec. 1998).

Ozaki et al., *New Stent Technologies*, Progress in Cardiovascular Diseases, vol. XXXIX(2):129-140 (Sep./Oct. 1996).

Parkell, Inc., *SNAP Powder-Liquid Temporary Crown and Bridge Resin*, http://www.parkell.com/snap.html, printed Oct. 21, 2004, 1 pg.

Parkell, Inc., *Material Safety Data Sheets*, http://www.parkell.com/msds.html, printed Oct. 21, 2004, 2 pgs.

Parkell, Inc., *MSDS No. S426, VAR*, Material Safety Sheet, 2 pgs (2002).

Parkell, Inc., MSDS No. S441, Material Safety Data Sheet, 2 pgs (2002).

Pechar et al., *Poly(ethylene glycol) Multiblock Copolymer as a Carrier of Anti-Cancer Drug Doxorubicin*, Bioconjucate Chemistry 11(2):131-139 (Mar./Apr. 2000).

Peng et al., *Role of polymers in improving the results of stenting in coronary arteries*, Biomaterials 17:685-694 (1996).

Porté-Durrieu et al., *Surface Treatment of Biomaterials by Gamma and Swift Heavy Ions Grafting*, Nuclear Instruments and Methods in Physics Research, vol. B 151, pp. 404-415 (1999).

Porté-Durrieu et al., *Development of "Heparin-Like" Polymers Using Swift Heavy Ion and Gamma Radiation. I. Preparation and Characterization of the Materials*, Surface Treatment of Biomaterials, pp. 119-127 (2000).
Revell et al., *Experimental Studies of the Biological Response to a New Bone Cement: II Soft Tissue Reactions in the Rat*, Clinical Materials, vol. 10, pp. 233-238 (1992).
Saotome, et al., *Novel Enzymatically Degradable Polymers Comprising α-Amino Acid, 1,2-Ethanediol, and Adipic Acid*, Chemistry Letters, pp. 21-24, (1991).
Shigeno, *Prevention of Cerebrovascular Spasm By Bosentan, Novel Endothelin Receptor*, Chemical Abstract 125:212307 (1996).
Techspray, Bulk Solvents, http://www.techspray.com/bulksup.htm, printed Sep. 21, 2004, 3 pages.
Techspray, *Flux Remover AMS*, Product Information, http://www.techspray.com/1665info.htm, printed Aug. 28, 2001, 2 pages.
Teomin et al., *Perivascular delivery of heparin for the reduction of smooth muscle cell proliferation after endothelial injury*, J. of Controlled Release, vol. 60, pp. 129-142 (1999).
Topol et al., *Frontiers in Interventional Cardiology*, Circulation, vol. 98, pp. 1802-1820 (1998).
Urban et al., *Why Make Monofilament Sutures Out of Polyvinylidene Fluoride?*, ASAIO J., vol. 40, No. 2, pp. 145-156 (1994).
Verweire et al., *Evaluation of fluorinated polymers as coronary stent coating*, J. Mater.Sci: Mater In Med., vol. 11, No. 4, pp. 207-212 (2000).
Weightman et al., *The Mechanical Properties of Cement and Loosening of the Femoral Component of Hip Replacements*, J. Bone and Joint Surg., vol. 69-B, No. 4, pp. 558-564 (Aug. 1987).
Wilensky et al., *Methods and Devices for Local Drug Delivery in Coronary and Peripheral Arteries*, Trends Cardiovasc. Med. 3(5):163-170 (1993).
Wholey et al., *Global Experience in Cervical Carotid Artery Stent Placement*, Catherization and Cardiovascular Inteventions, vol. 50, No. 2, pp. 160-167 (2000).
Woo et al., *Phase Behavior of Polycarbonate Blends with Selected Halogenated Polymers*, J. Appl. Polym. Sci., vol. 30, pp. 4243-4249 (1985).
Yokoyama et al., *Characterization of Physical entrapment and chemical conjugation of adriamycin in polymeric micelles and their design for in vivo delivery to a solid tumor*, Journal of Controlled Release 50:79-92 (1998).
International Search Report for PCT appl. PCT/US03/15347, filed May 14, 2003, date of mailing Sep. 4, 2003, 6 pgs.
International Search Report for PCT appl. PCT/US03/15544, filed May 14, 2003, date of mailing Jan. 23, 2004, 9 pgs.
International Search Report for PCT appl. PCT/US03/28643, filed Sep. 10, 2003, date of mailing Mar. 12, 2003, 10 pgs.
International Search Report for PCT appl. PCT/US03/21170, filed Jul. 2, 2003, date of mailing Oct. 31, 2003, 8 pgs.
Anderson et al., *Nitric-Oxide and Nitrovasodilators: Similarities, Differences and Potential Interactions*, JACC 24(2):555-566 (1994).
Anderson et al., *Close Relation of Endothelial Function in the Human Coronary and Peripheral Circulations*, JACC 26(5):1235-1241 (1995).
Bode-Boger et al., *Elevated L-Arginine/Dimethylarginine Ratio Contributes to Enhanced Systemic NO Production by Dietary L-Arginine in Hypercholesterolemic Rabbits*, Biochem. And Biophys. Res. Comm. 219:598-603 (1996).
Bodmer et al., *Enhanced Recognition of a Modified Peptide Antigen by Cytotoxic T Cells Specific for Influenza Nucleoprotein*, Cell 52:253-258 (1988).
Boger et al., *An Endogenous Inhibitor of Nitric Oxide Synthase Regulates Endothelial Adhesiveness for Monocytes*, JACC 36(7):2287-2295 (2000).
Boger et al., *Asymmetric Dimethylarginine (ADMA):A Novel Risk Factor for Endothelial Dysfunction: Its Role in Hypercholesterolemia*, Circ. 98:1842-1847 (1998).
Boger et al., *Asymmetric Dimethylarginine: A Novel Risk Factor for Endothelial Dysfunction*, Circ. 96(8):I-32 (1997).
Boger et al., *The Endogenous NO Synthase Inhibitor Asymmetric Dimethyl-L-Arginine (ADMA) Regulates Endothelial NO Production and Adhesiveness for Monocytes* (Abstract J5), Nitric Oxide 2:126 (1998).
Boger et al., *Restoring Vascular Nitric Oxide Formation by L-Arginine Improves the Symptoms of Intermittent Claudication in Patients With Peripheral Arterial Occlusive Disease*, J. Am. Coll. Cardiol. 32:1336-1344 (1998).
Candipan et al., *Dietary L-Arginine Attenuates Macrophage Infiltration and Intimal Hyperplasia After Balloon Injury* (Abstract 765-2), JACC 25:275A (1995).
Candipan et al., *Regression or Progression: Dependency on Vascular Nitric Oxide*, Arterioscler. Thromb. Vasc. Biol. 16(1):44-50 (1996).
Chan et al., *Asymmetric Dimethylarginine Increases Mononuclear Cell Adhesiveness in Hypercholesterolemic Humans*, Arterioscler. Thromb. Vasc. Biol. 20:1040-1046 (2002).
Cooke et al., *Arginine: A New Therapy for Atherosclerosis?* Circ. 95(2):311-312 (1997).
Cooke et al., *Cytoprotective Effects of Nitric Oxide*, Circ. 88(5)1:2451-2454 (1993).
Cooke et al., *Derangements of the Nitric Oxide Synthase Pathway, L-Arginine, and Cardiovascular Diseases*, Circ. 96(2):379-382 (1997).
Cooke et al., *Diffuse Coronary Artery Disease and Endothelial Dysfunction: Form Follows Function*, ACC Curr. J. Rev. pp. 19-25 (Nov./Dec. 2000).
Cooke et al., *Regression and Progression: Dependency Upon NO* (Abstract), J. Investi. Med. 43(2) Suppl. 2:211A (1995).
Cooke et al., *The Role of Endothelium-Derived Nitric Oxide in Atherosclerosis*, Adv. Vasc. Path. 1150:3-14 (1997).
Cooke, *Does ADMA Cause Endothelial Dysfunction?*, Arterioscler. Thromb. Vasc. Biol. 20:2032-2037 (2002).
Cooke, *Enhancement of Endogenous Vascular Nitric Oxide: A New Therapeutic Strategy for Restenosis* (Abstract 301), Eur. J. Clin. Investi. 28:A53 (1998).
Cooke, *Is Atherosclerosis an Arginine Deficiency Disease?*, J. Investi. Med. 46(8):377-380 (1998).
Cook, *Nutriceuticals for Cardiovascular Health*, Am. J. Cardio., 82(10A):43S-46S (1998).
Cooke, *Role of Nitric Oxide in Progression and Regression of Atherosclerosis*, West. J. Med. 164(5):419-424 (1996).
Cooke, *The 1998 Nobel Prize in Medicine: Clinical Implications for 1999 and Beyond*, Vasc. Med. 4:57-60 (1999).
Cooke, *The Endothelium: A New Target for Therapy*, Vasc. Med. 5:49-43 (2000).
Cooke, *The Pathophysiology Of Peripheral Arterial Disease: Rational Targets for Drug Intervention*, Vasc. Med. 2:227-230 (1997).
Creager et al., *L-Arginine Improves Endothelium-Dependent Vasodilation in Hypercholesterolemic Humans*, J. Clin. Investi. 90:1248-1253 (1992).
Drexler et al., *Effect of L-Arginine on Coronary Endothelial Function in Cardiac Transplant Recipients: Relation to Vessel Wall Morphology*, Circ. 89(4):1615-1623 (1994).
Drexler et al., *Endothelial Dysfunction in the Coronary Circulation After Cardiac Transplantation: Effect of L-Arginine* (Abstract I356), Circ. 86(4) Supp: 1418 (1992).
Dulak et al., *Nitric Oxide Induces the Synthesis of Vascular Endothelial Growth Factor by Rat Vascular Smooth Muscle Cells*, Arterioscler. Thromb. Vasc. Biol. 20:659-666 (2002).
http://www.lf2.cuni.dz/physiolres/1997/issue5/iss5cl6.html,
Farghali et al., *Effects of Nitroprusside as a Nitric Oxide Donor on Anoxia/Reoxygenation and D-galactosamine Hepatic Injuries: a Study in Perfused Hepatocytes* (Summary), Physiol. Res. 46(5):363-369 (1997).
Gaiser et al., *Lethal Short-Limbed Dwarfism in Transgenic Mice with an Arginine to Cysteine Substitution in Alpha-I (II) Procollagen* (Abstract 3369), Mol. Biol. Cell 7:579A (1996).
Ganz et al., *Coronary Vasospasm in Humans—The Role of Atherosclerosis and of Impaired Endothelial Vasodilator Function*, Basic Res. Cardiol. 86(Suppl 2):215-222 (1991).
Gregory et al., *Enhanced Nitric Oxide Production Induced by the Administration of L-Arginine Does Not Inhibit Arterial Neointimal*

Formation After Overwhelming Alloimmune Injury, J. Heart Lung Transplant. 15(1)Part 1:58-66 (1996).

Gregory et al., *Nitric Oxide Induced by the Administration of L-Arginine Does Not Inhibit Arterial Neointimal Formation Following Alloimmune Injury* (Abstract 41), J. Heart Lung Transplant. 14(1)Part 2:S45 (1995).

Heeschen et al., *Hypercholesterolemia Impairs Angiogenic Response to Hind Limb Ischemia: Role of ADMA* (Abstract 2490), Circ. I-473 (1999).

Ho et al., *Dietary L-Arginine Reverses the Inhibitory Effect of Asymmetric Dimethylarginine on Angiogenesis in Hypercholesterolemia* (Abstract 407-2), JACC 33:1A (1999).

Huet et al., *Structural Homologies Between Two HLA B27-Restricted Peptides Suggest Residues Important for Interaction with HLA B27*, Intl. Immunol. 2(4):311-316 (1990).

Hutchison et al., *Effects of L-Arginine on Atherogenesis and Endothelial Dysfunction Due to Secondhand Smoke*, Hyperten. 34:44-50 (1999).

Jang et al., *Angiogenesis is Impaired by Hypercholesterolemia: Role of Asymmetric Dimethylarginine*, Circ. 102:1414-1419 (2000).

Jang et al., *L-Arginine Reverses the Anti-Angiogenic Effects of Asymmetric Dimethylarginine* (Abstract), J. Investi. Med. 4(2):86A (1999).

Jozkowicz et al., *Genetic Augmentation of Nitric Oxide Synthase Increases the Vascular Generation of VEGF*, Cardiovasc. Res. 51:773-783 (2001).

Kown et al., *Arginine Polymers Inhibit Graft Coronary Artery Disease Following Cardiac Transplantation* (Abstract 726), Transplant. 69(8):S300 (2000).

Kown et al., *L-Arginine Polymers Inhibit the Development of Vein Graft Neointimal Hyperplasia*, J. Thorac. Cardiovasc. Surg. 121(5):971-980 (2001).

Kown et al., *L-Arginine Polymer Mediated Inhibition of Graft Coronary Artery Disease After Cardiac Transplantation*, Transplant. 71(11):1542-1548 (2001).

Krejcy et al., *Distribution and Metabolism of $N^G$-Nitro-L-Arginine and $N^G$-Nitro-L-Arginine Methylester in Canine Blood* in vitro, Naunyn-Schmiedeberg's Arch. of Pharmacol. 347(3):342-345 (1993).

Krejcy et al., *Metabolism of L-$N^G$-Nitro Arginine Methyl Ester in Human and Canine Plasma* (Abstract 207), J. Mol. Cell. Cardiol. 24(Supp IV):S108 (1992).

Kyte et al., *A Simple Method for Displaying the Hydropathic Character of a Protein*, J. Mol. Biol. 157:105-132 (1982).

Latron et al., *Positioning of a Peptide in the Cleft of HLA-A2 by Complementing Amino Acid Changes*, PNAS 88:11325-11329 (1991).

Lieberman et al., *Estrogen Improves Endothelium-Dependent, Flow-Mediated Vasodilation in Postmenopausal Women*, Annals Intern. Med. 121(12):936-941 (1994).

Lieberman et al., *Flow-Induced Vasodilation of the Human Brachial Artery is Impaired in Patients Years of Age with Coronary Artery Disease*, Am. J. Cardiol. 78:1210-1214 (1996).

Lim et al., *Acute Local Delivery of L-Arginine Reduces Long Term Intimal Thickening and Macrophage Infiltration* (Abstract 2346), Circ. 94(8):I403 (1996).

Lin et al., *Addition of a Poly Arginine Linker to Cyclosporin A Facilitates Transcutaneous Delivery and Topical Inhibition of Cutaneous Inflammation* (Abstract 155), J. Inv. Derm. 114(4):777 (2000).

Lissin et al., *Maintaining the Endothelium: Preventive Strategies for Vessel Integrity*, Prev. Cardio. 3:172-177 (2000).

Maxwell et al., *A Medical Food Designed to Enhance Nitric Oxide Activity Restores Endothelium-Dependent Function in Hypercholesterolemia* (Abstract 140), Nitric Oxide: Biology and Chemistry 4(3):251(2000).

Maxwell et al., *A Nutritional Product Designed to Enhance Nitric Oxide Activity Restores Endothelium-Dependent Function in Hypercholesterolemia*, J. Investi. Med. 47(2):45A (1999).

Maxwell et al., *Cardiovascular Effects of L-Arginine*, Curr. Opin. Nephrol. Hyperten. 7:63-70 (1998).

Maxwell et al., *Endothelial Dysfunction in Hypercholesterolemia is Reversed by a Nutritional Product Designed to Enhance Nitric Oxide Activity*, Cardiovasc. Drugs Therapy 14:309-316 (2000).

Maxwell et al., *Improvement in Walking Distance and Quality of Life in Peripheral Arterial Disease by a Medical Food* (Abstract 86), Nitric Oxide: Biology and Chemistry, 4(3):232 (2000).

Maxwell et al., *Improvement in Walking Distance and Quality of Life in Peripheral Arterial Disease by a Nutritional Product Designed to Enhance Nitric Oxide Activity* (Abstract), J. Investi. Med. 47(2):63A (1999).

Maxwell et al., *L-Arginine Attenuates the Impairment in Exercise Capacity Due to Hypercholesterolemia* (Abstract), JACC 29:265A (1997).

Maxwell et al., *L-Arginine Enhances Aerobic Exercisae Capacity in Association with Augmented Nitric Oxide Production*, J. Appl. Physiol. 90:933-938 (2001).

Maxwell et al., *Limb Blood Flow During Exercise is Dependent on Nitric Oxide*, Circ. 98:369-374 (1998).

Maxwell et al., *Modulation of the Nitric Oxide Synthase Pathway in Atherosclerosis*, Exp. Physiol. 83:573-584 (1998).

Maxwell et al., *Nutritional Therapy for Peripheral Arterial Disease: A Double-Blind, Placebo-Controlled, Randomized Trial of HeartBar®*, Vasc. Med. 5:11-19 (2000).

Maxwell et al., *The Role of Nitric Oxide in Atherosclerosis*, Cor. Art. Dis. 10:277-286 (1999).

Meredith et al., *Role of Endothelium in Ischemic Coronary Syndromes*, Am. J. Cardiol. 72(8):27C-32C (1993).

Meredith et al., *Role of Impaired Endothelium-Dependent Vasodilation in Ischemic Manifestations of Coronary Artery Disease*, Circ. 87(5) Suppl:V56-V66 (1993).

Mitchell et al.; *Polyarginine Enters Cells More Efficiently than Other Polycationic Homopolymers*, J. Peptide Res. 56:318-325 (2000).

Miyazaki et al., *Endogenous Nitric Oxide Synthase Inhibitor: A Novel Marker of Atherosclerosis*, Circ. 99:1141-1146 (1999).

http://pysiology.cup.cam.ac.uk/Proceedings/Abstracts/523P/Birmingham/Files/S32.html, Musialek et al., *The Nitric Oxide Donor Sodium Nitroprusside Increases Heart Rate In The Absence Of Changes In Arterial Blood Pressure When Applied Topically To The Sino-Atrial Node In The Anaesthetized Pig*, J. Physiol. (2000), printed Jun. 12, 2001.

Niebauer et al., *Effects of Chronic Exercise in Patients with Chronic Heart Failure on Markers of Oxidative Stress* (Abstract 1019-10), JACC 33:172A (1999).

Niebauer et al., *Endothelium-Derived Nitric Oxide Attenuates Monocyte-Endothelial Interaction in Chronic Hypercholesterolemia* (Abstract 2014) Circ. 92(8)Suppl I:I-422 (1995).

Niebauer et al., *Endotoxin and Immune Activation in Chronic Heart Failure: A Prospective Cohort Study*, Lancet 353:1838-1842 (1999).

Niebauer et al., *Gene Transfer of Nitric Oxide Synthase: Effects on Endothelial Biology*, JACC 34(4):1201-1207 (1999).

Niebauer et al., *Local Delivery of L-Arginine After Balloon Angioplasty: Time Course of Intramural L-Arginine Activity, Nitric Oxide Production and Monocyte Binding* (Abstract 3082), Circ. 96:I-551 (1997).

Niebauer et al., *Local L-Arginine Delivery After Balloon Angioplasty Reduces Monocyte Binding and Induces Apoptosis*, Circ. 100:1830-1835 (1999).

Niebauer et al., *Oxidative Stress in Chronic Health Failure: Effects of Exercise* (Abstract P1652), Eur. Heart J. 20:305 (1999).

Niebauer et al., *Time Course of Intramural L-Arginine Activity, Nitric Oxide Production and Monocyte Binding Following Local L-Arginine Delivery After Balloon Angioplasty* (Abstract 251), Eur. Heart J. 19:14 (1998).

Ohno et al., *Shear Stress Elevates Endothelial cGMP: Role of a Potassium Channel and G Protein Coupling*, Circ. 88:193-197 (1993).

Raby et al., *Changing Vasomotor Responses of Coronary Arteries to Nifedipine*, Am. Heart J. 126(2):333-338 (1993).

Rothbard et al., *Conjugation of Arginine Oligomers to Cyclosporin A Facilitates Topical Delivery and Inhibition of Inflammation*, Nature Med. 6(11):1253-1257 (2000).
Rothbard et al., *Molecular Transporters Facilitate Topical Protein Transduction Into the Skin* (Abstract 957), J. Investi. Derm. 117(2):549 (2001).
Rothbard et al., *Reversal of HLA Restriction by a Point Mutation in an Antigenic Peptide*, Intl. Immunol. 1(4):487-495 (1989).
Safai et al., *L-Arginine/Nitric Oxide Pathway and Glomerular Injury in Preeclampsia* (Abstract A0504), J. Am. Soc. Nephrol. 9:98A (1998).
Schoolnik et al., *Gonococcal Pili: Primary Structure and Receptor Binding Domain*, J. Exp. Med. 159:1351-1370 (1984).
Schwarzacher et al., *L-$N^G$-Nitro-Arginine Methyl Ester in the Anesthetized Rabbit: Venous Vasomotion and Plasma Levels*, J. Vasc. Res. 29(3):290-292.
Schwarzacher et al., *Acute Local Delivery of L-Arginine Reduces Intimal Thickening and Macrophage Infiltration Following Balloon Injury in the Rabbit* (Abstract 2926), Eur. Heart J. 17:527 (1996).
Schwarzacher et al., *Assessment of Changes in Vasomotor Tone* in vivo *Using Intravascular Ultrasound*, J. Pharmacol. Toxicol. Meth. 28(3):143-147 (1992).
Schwarzacher et al., *Blockade of Endothelium-Derived Relaxing Factor Synthesis with $N^G$-Nitro-L-Arginine Methyl Ester Leads to Enhanced Venous Reactivity* in vivo, Eur. J. Pharmacol. 229(2/3):253-258 (1992).
Schwarzacher et al., *Local Delivery of L-Arginine Increases Vascular Nitric Oxide Production and Improves Endothelium-Dependent Vasomotion* (Abstract P492), Eur. Heart J. 17:82 (1996).
Schwarzacher et al., *Local Delivery of L-Arginine Increases Vascular Nitric Oxide Production and Improves Endothelium Dependent Vasomotion* (Abstract 779-6), JACC 27(2) Suppl IA:288A (1996).
Schwarzacher et al., *Local Intramural Delivery of L-Arginine Enhances Nitric Oxide Generation and Inhibits Lesion Formation After Balloon Angioplasty*, Circ. 95(7):1863-1869 (1997).
Schwarzacher, *New Therapeutic Approaches for Correction of Endothelial Function After Balloon Dilatation* (Eng. Abstract), J Kardiologie 7(1):14-17 (2000).
Schwarzacher et al., *Altered Reactivity of the Inferior Vena Cava to Noradrenaline and Acetylcholine Following the Blockade of EDRF-Biosynthesis with $N^G$-Nitro-$_L$-Arginine Methyl Ester*, Clin. Exp. Pharmacol. Physiol. 23(6/7):490-492.
Selwyn et al., *Pathophysiology of Ischemia in Patients with Coronary Artery Disease*, Prog. Cardiovasc. Dis. XXXV(1):27-39 (1992).
http://www.pharmsci.org/scientificjournals/pharmsci/journal/99_7.html, Shameem et al., *A Short Term (Accelerated Release) Approach to Evaluate Peptide Release from PLGA Depot-Formulations* Published Jul. 21, 1999, printed Feb. 19, 2002.
Sievers et al., *Low-Temperature Manufacturing of Fine Pharmaceutical Powders with Supercritical Fluid Aerosolization in a Bubble Dryer®*, Pure Appl. Chem. 73(8):1299-1303 (2001).
Singer et al., *Anti-Atherogenic Effect of the EDRF Precursor* (Abstract I20), Circ. 86(4) Suppl:78 (1992).
Singer et al., *Chronic Supplementation with L-Arginine, the Precursor of Endogenous Nitric Oxide, Causes Tolerance to Nitroglycerin*, Circ. 86(4) Suppl:1942 (1992).
Singer et al., *Dietary Supplements of L-Arginine Reduce Atherogenesis and Alter Vascular Reactivity in Hypercholesterolemic Animals* (Abstract) Clin. Res. 41(1):78A (1993).
Singer et al., *Discordant Effects of Dietary L-Arginine on Vascular Structure and Reactivity in Hypercholesterolemic Rabbits*, J. Cardiovasc. Pharmacol. 25:710-716 (1995).
Stuehlinger et al., *Homocysteine Induced Accumulation of Asymmetric Dimethylarginine—Role of DDAH and Effect of Antioxidants* (Abstract 854), Circ. 102:II-177 (2000).
Suzuki et al., *Can Local Delivery of L-Arginine Reduce In-Stent Restenosis in Humans? An Ultrasound Volumetric Analysis* (Abstract 2459), Circ. 100(18) Suppl. I:I466-I467 (1999).
Tangphao et al., *Diurnal Variation of Plasma L-Arginine Concentrations and The Effect of Dietary L-Arginine Intake* (Abstract PII-25), Clin. Pharmacol. Therapeu. 63:178 (1998).
Tangphao et al., *L-Arginine and Nitric Oxide-Related Compounds in Plasma: Comparison of Normal and Arginine-Free Diets in a 24-h Crossover Study*, Vasc. Med. 4:27-32 (1999).
Theilmeier et al., *Adhesiveness of Mononuclear Cells in Hypercholesterolemic Humans in Normalized by Dietary L-Arginine*, Arterioscler. Thromb. Vasc. Biol. 17(12):3557-3564 (1997).
Theilmeier et al., *Adhesiveness of Mononuclear Cells is Increased in Hypercholesterolemic Humans, and Reduced by The NO Precursor* (Abstract 765-4), JACC 25:276A (1995).
Todd et al., *Regulation of Loblolly Pine (Pinus taeda L.) Arginase in Developing Seedling Tissue During Germination and Post-Germinative Growth*, Plant Mol. Biol. 45:555-565 (2001).
Tsao et al., *Anti-Platelet Effect of Dietary L-Arginine, the Nitric Oxide Precursor* (Abstract 732-6), JACC 21(2):Suppl A:125A (1993).
Tsao et al., *Dietary Arginine Alters Endothelial Adhesiveness via NO* (Abstract), Clin. Res. 42(2):175A (1994).
Tsao et al., *Dietary L-Arginine Reduces Platelet Reactivity in Hypercholesterolemic Rabbits* (Abstract), Clin. Res. 41(1):78A (1993).
Tsao et al., *Endothelial Alterations in Hypercholesterolemia: More Than Simply Vasodilator Dysfunction*, J. Cardiovasc. Pharmacol. 32(Suppl 3):S48-S53 (1998).
Tsao et al., *Enhanced Endothelial Adhesiveness in Hypercholesterolemia is Attenuated by L-Arginine*, Circ. 89:2176-2182 (1994).
Tsao et al., *Exposure to Shear Stress Alters Endothelial Adhesiveness: Role of Nitric Oxide*, Circ. 92(12):3513-3519 (1995).
Tsao et al., *Fluid Flow Inhibits Endothelial Adhesiveness: Nitric Oxide and Transcriptional Regulation of VCAM-1*, Circ. 94(7):1682-1689 (1996).
Tsao et al., *L-Arginine Attenuates Platelet Reactivity in Hypercholesterolemic Rabbits*, Arterioscler. Thromb. 14(10):1529-1533 (1994).
Tsao et al., *Nitric Oxide Regulates Monocyte Chemotactic Protein-1*, Circ. 96(3):934-940 (1997).
Uemura et al., *Rapid and Efficient Vascular Transport of Arginine Polymers Inhibits Myointimal Hyperplasia*, Circ. 102:2629-2635 (2000).
Uemura et al., *Short Polymers of Arginine Inhibit Myointimal Hyperplasia: Efficient Intracellular Translocation and Activation of Nitric Oxide Synthesis* (Abstract 411-2), JACC pp. 548A-549A (2000).
Uemura et al., *Short Polymers of Arginine Rapidly Translocate into Vascular Cells: Effect on Nitric Oxide Synthesis* (Abstract 64), Circ. 102(18) Suppl II:II-16 (2000).
Vita et al., *Patients with Evidence of Coronary Endothelial Dysfunction as Assessed by Acetylcholine Infusion Demonstrate Marked Increase in Sensitivity to Constrictor Effects of Catecholamines*, Circ. 85(4):1390-1397 (1992).
von der Leyen et al., *Gene Therapy Inhibiting Neointimal Vascular Lesion:* in vivo *Transfer of Endothelial Cell Nitric Oxide Synthase Gene*, PNAS 92:1137-1141 (1995).
von der Leyen et al., *Overexpression of Constitutive, Endothelial-Type Nitric Oxide Synthase As an* in vivo *Gene Transfer Approach to Prevent Neointima Formation After Vascular Injury*, Clin. Res. 42(2):180A (1994).
Walls et al., *Effects of Growth Factors and L-Arginine on Ischemic Skin Flaps in Rats*, Vet. Surg. 24:484-491 (1995).
Wang et al., *Arginine Prevents Atherogenesis in the Coronary Artery of the Hypercholesterolemic Rabbit* (Abstract 732-2), JACC 21(2) Suppl A:124A (1993).
Wang et al., *Arginine Restores Nitric Oxide Activity and Inhibits Monocyte Accumulation After Vascular Injury in Hypercholesterolemic Rabbits*, JACC 28(6):1573-1579 (1996).
Wang et al., *Dietary Arginine Prevents Atherogenesis in the Coronary Artery of the Hypercholesterolemic Rabbit*, JACC 23(2):452-458 (1994).

Wang et al., *Regression of Atherosclerosis: Role of Nitric Oxide and Apoptosis*, Circ. 99:1236-1241 (1999).

Wender et al., *An Efficient, Scalable Synthesis of the Molecular Transporter Octaarginine via a Segment Doubling Strategy*, Org. Letts. 3(21):3229-3232 (2001).

Wender et al., *The Design, Synthesis, and Evaluation of Molecules that Enable or Enhance Cellular Uptake: Peptoid Molecular Transporters*, PNAS 97(24):13003-13008 (2000).

Wolf et al., *Dietary L-Arginine Supplementation Normalizes Platelet Aggregation in Hypercholesterolemic Humans*, JACC 29(3):479-485 (1997).

Wong et al., *Antiatherogenic Effects of Dietary L-Arginine in the Systemic and Pulmonary Circulations in the Hypercholesterolemic Rabbit* (Abstract) Clin. Res. 41(2):212A (1993).

Yeung et al., *Interactions Between Mental Stress and Coronary Endothelial Dysfunction*, Homeostasis 34(5-6):244-251 (1993).

Yeung et al., *The Effect of Atherosclerosis on the Vasomotor Response of Coronary Arteries to Mental Stress*, N. Eng. J. Med. 325(22):1551-1556 (1991).

Zalpour et al., *Platelet Hyperaggregability in Hypercholesterolemic Humans: Reversal by Dietary L-Arginine* (Abstract 765-1), JACC p. 275A (1995).

Brochure, FreeZone CFC-Free Freeze Dry Systems, A Complete Guide to Laboratory Lyophilization Products, LABCONCO (2000).

http://www.temcoinstruments.com/product.html, Temco Instruments product information, *New Process for Rapid Micronization and Drying of Proteins, Pharmaceuticals and Other Particles*, printed Feb. 26, 2002.

http://www.uspharmacist.com/NewLook/CE/larginine/lesson.cfm, *The Role of L-Arginine In Cardiovascular Health*, U.S. Pharmacist Continuing Education, printed Sep. 12, 2002.

\* cited by examiner

COATINGS CONTAINING POLYCATIONIC PEPTIDES FOR CARDIOVASCULAR THERAPY

BACKGROUND OF THE INVENTION

1. Field of the Invention

This invention relates to the field of medical devices, especially devices used for delivery of drugs. Particularly, this invention is directed to coatings for drug delivery devices, such as drug eluting vascular stents. More particularly, this invention is directed to coatings which include polycationic peptides such as polymers and/or oligomers of L-arginine.

2. Description of the State of the Art

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against the atherosclerotic plaque of the lesion to remodel the lumen wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, a stent is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically, stents are capable of being compressed, so that they can be inserted through small vessels via catheters, and then expanded to a larger diameter once they are at the desired location. Examples in patent literature disclosing stents which have been applied in PTCA procedures include stents illustrated in U.S. Pat. No. 4,733, 665 issued to Palmaz, U.S. Pat. No. 4,800,882 issued to Gianturco, and U.S. Pat. No. 4,886,062 issued to Wiktor.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results. One proposed method for medicating stents involves the use of a polymeric carrier coated onto the surface of a stent. A solution which includes a solvent, a polymer dissolved in the solvent, and a therapeutic substance dispersed in the blend is applied to the stent. The solvent is allowed to evaporate, leaving on the stent surface a coating of the polymer and the therapeutic substance impregnated in the polymer.

Local administration of therapeutic agents via stents has shown some favorable results in reducing restenosis. However, development of restenosis remains a persistent problem which has not been significantly alleviated by therapeutic substances which are currently used in the market. Accordingly, there is a great need for better and more effective therapeutic compositions, and methods of administering the compositions, for the effective treatment of restenosis.

SUMMARY

A coating for an implantable medical device, such as a stent, is disclosed. The coating comprises a region including a polycationic peptide and a region free from any polycationic peptides. The polycationic peptide can be poly(L-arginine), poly(D-arginine), poly(D,L-arginine), poly(L-lysine), poly(D-lysine), poly(δ-guanidino-α-aminobutyric acid), and a racemic mixture of poly(L-arginine) or poly(D-arginine). In one embodiment, the region including the polycationic peptide includes a hydrogel containing the polycationic peptide. The hydrogel can be fabricated of substances comprising carboxylated hydrocarbons, polycationic compounds, polyanionic compounds and mixtures thereof. In one embodiment, the region free from the polycationic peptide is positioned on the surface of the device and beneath the region including the polycationic peptide. In an alternative embodiment, the polycationic peptide can be encapsulated in particles in the coating.

A method for fabricating a coating for an implantable medical device, such as a stent, is also disclosed. The method comprises forming a coating on the device, the coating including a polycationic peptide; and treating the coating with a stimulus for enriching a region close to the outer surface of the coating with the polycationic peptide. In one embodiment, the treatment of the coating includes subjecting the device to a humid environment at a selected temperature, for example about 50° C. at a humidity of about 100%. In another embodiment, the treatment can include subjecting the device to an electronic beam or to autoclaving.

A method of modifying a coating for an implantable medical device is disclosed. The method comprises exposing the coating, including a polycationic peptide to ethylene oxide at a selected temperature and conjugating poly(ethylene glycol) to the coating.

A method of fabricating a coating for a medical device is disclosed. The method comprises forming a coating on the device, the coating including a polycationic peptide, and causing some of the bonds of the peptide to be cleaved for increasing the population of the peptide in the coating.

A stent comprising a coating is also disclosed wherein the coating includes a peptide such that the population of the peptide is greater in the outermost region of the coating.

A method of fabricating a coated stent is also disclosed, comprising forming a coating on the stent wherein the coating includes a region containing a peptide and a region free from any peptides.

DETAILED DESCRIPTION

The stent coating according to the embodiments of the present invention may have any one or combination of the following layers or regions in addition to the reservoir layer containing a therapeutic substance: a primer layer, a topcoat layer, and a finishing coat layer. The optional finishing coat layer may also include a drug or a therapeutic substance. The reservoir layer can be applied directly onto the stent surface, or optionally on the primer layer. The optional finishing coat layer can be applied on the topcoat layer and, when present, can be the outermost region of the stent coating. Subsequent to the implantation of the stent, the reservoir layer gradually releases the therapeutic substance.

One example of a drug or therapeutic substance that can be used is a polycationic peptide or a mixture of several polycationic peptides. Representative examples of suitable polycationic peptides include poly(L-arginine), poly(D-arginine), poly(D,L-arginine), poly(L-lysine), poly(D-lysine), poly(δ-guanidino-α-aminobutyric acid), racemic mixtures of poly(L-arginine) and poly(D-arginine), chitosan, and mixtures thereof. L-arginine, also known as R or 2-amino-5-guanidinovaleric acid, is an amino acid having a formula NH=C(NH$_2$)—NH—CH$_2$—CH$_2$—CH$_2$—CH(NH$_2$)—COOH. Polymers and/or oligomers of L-, D-, and/or D,L-arginine that can be used are referred to in the present application as "PArg" and comprise a plurality of repeating monomeric amino acid units connected with peptide bonds. PArg has a general formula

$$H[NH—CHX—CO]_p—OH \quad (I)$$

where "p" can be within a range of 5 and 1,000, or, within a range of between 6 and 20. For example, a heptamer (R7) (p=7), or a nonamer (R9) (p=9), can be used.

In formula (I), "X" represents 1-guanidinopropyl radical having the structure —CH$_2$—CH$_2$—CH$_2$—NH—C(NH$_2$)=NH. The terms "polymers and/or oligomers of D-, L-, and/or D, L-arginine," "poly(L-arginine)," "poly(D-arginine)," "poly(D,L-arginine)," and "PArg" used in the present application are intended to include L-, D-, and/or D,L-arginine in both its polymeric and oligomeric form.

Poly(ethylene-co-vinyl alcohol) (EVAL) is one example of a polymer that can be used for any of the coating layers. EVAL is a product of hydrolysis of ethylene-vinyl acetate copolymers and has the general formula —[CH$_2$—CH$_2$]$_m$—[CH$_2$—CH(OH)]$_n$—. EVAL may also include a terpolymer having up to about 5 molar % of units derived from styrene, propylene and other suitable unsaturated monomers. A brand of copolymer of ethylene and vinyl alcohol distributed commercially under the trade name EVAL by Aldrich Chemical Co. of Milwaukee, Wis., can be used.

Other examples of polymers that can be used include polyacrylates, such as poly(butyl methacrylate) (PBMA), poly(ethyl methacrylate) (PEMA), and poly(ethyl methacrylate-co-butyl methacrylate) [P(EMA-BMA)]; fluorinated polymers and/or copolymers, such as poly(vinylidene fluoride) (PVDF) and poly(vinylidene fluoride-co-hexafluoro propene) (PVDF-HFP); and blends of polyacrylates and fluorinated polymers and/or copolymers. One example of the blend of a polyacrylate and a fluorinated polymer that can be used can contain between about 10 and about 95% (mass) of the fluorinated polymer.

Representative examples of other suitable polymers include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly (amino acids), cyanoacrylates, poly(trimethylene carbonate), poly(iminocarbonate), co-poly(ether-esters) (e.g. PEO/PLA), polyalkylene oxalates, polyphosphazenes, biomolecules (such as fibrin, fibrinogen, cellulose, starch, collagen and hyaluronic acid), polyurethanes, silicones, polyesters, polyolefins, polyisobutylene and ethylene-alpha-olefin copolymers, vinyl halide polymers and copolymers (such as polyvinyl chloride), polyvinyl ethers (such as polyvinyl methyl ether), polyvinylidene chloride, polyacrylonitrile, polyvinyl ketones, polyvinyl aromatics (such as polystyrene), polyvinyl esters (such as polyvinyl acetate), copolymers of vinyl monomers with each other and olefins (such as ethylene-methyl methacrylate copolymers, acrylonitrile-styrene copolymers, ABS resins, and ethylene-vinyl acetate copolymers), polyamides (such as Nylon 66 and polycaprolactam), alkyd resins, polycarbonates, polyoxymethylenes, polyimides, polyethers, epoxy resins, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

A. A Solution or Suspension Method for Incorporating PArg into Stent Coatings

The coating can be formed on the stent by dissolving the polymer in a solvent, or a mixture of solvents, and applying the resulting polymer solution on the stent by spraying or immersing the stent in the solution. To incorporate PArg into the reservoir layer and/or the optional finishing coat layer, PArg in a form of a solution can be combined with the polymer solution.

Representative examples of some solvents suitable for making the polymer solution include N,N-dimethylacetamide (DMAC), N,N-dimethylformamide (DMF), tetrahydrofurane (THF), cyclohexanone, xylene, toluene, acetone, i-propanol, methyl ethyl ketone, propylene glycol monomethyl ether, methyl butyl ketone, ethyl acetate, n-butyl acetate, and dioxane. Some solvent mixtures can be used as well. Representative examples of the mixtures include:

(1) DMAC and methanol (e.g., 50:50 by mass mixture);

(2) water, i-propanol, and DMAC (e.g., 10:3:87 by mass mixture);

(3) i-propanol, and DMAC (e.g., 80:20, 50:50, or 20:80 by mass mixtures);

(4) acetone and cyclohexanone (e.g., 80:20, 50:50, or 20:80 by mass mixtures);

(5) acetone and xylene (e.g. 50:50 by mass mixture); and (6) acetone, FLUX REMOVER AMS, and xylene (e.g., 10:50:40 by mass mixture).

FLUX REMOVER AMS is the trade name of a solvent manufactured by Tech Spray, Inc. of Amarillo, Tex. comprising about 93.7% of a mixture of 3,3-dichloro-1,1,1,2,2-pentafluoropropane and 1,3-dichloro-1,1,2,2,3-pentafluoropropane, and the balance of methanol, with trace amounts of nitromethane. Those having ordinary skill in the art will select the solvent or a mixture of solvents suitable for a particular polymer being dissolved.

Instead of introducing PArg in a solution, PArg can be introduced as a colloid system, such as a suspension in an appropriate solvent phase. The suspension can be mixed with a polymer solution. One example of the solvent phase can be a mixture of water, i-propanol and DMAC, containing between about 3 and 6 mass % of water, between about 18 and 19% of i-propanol, and the balance, DMAC solvent.

After the stent coating has been formed, the stent can then be additionally treated to enrich the surface with PArg. Various techniques of treatment can be used depending on the kind of PArg and whether a finishing coat layer is used.

In one embodiment, the coated stent can be exposed to the environment of a humidifying chamber. This treatment is particularly useful for R7 or R9. The length of such treatment can be, for example, about 24 hours, at a temperature of about 50° C. and relative humidity of about 100%. Any commercially available chamber can be used. As a result of the exposure of the stent to high humidity levels at elevated temperatures, the outermost surface of the coating is enriched with the peptide (e.g., R7 or R9).

If the finishing coat layer is not used, the stent can be treated after the reservoir layer containing the peptide (e.g., R7 or R9) has been applied, but prior to applying the topcoat layer. Consequently, as a result of the treatment, the surface of the drug-polymer layer gets enriched with the R7 or R9, followed by fabrication of the topcoat layer.

In another embodiment of the invention, the coated stent can be treated with high energy electronic beams. This method of treatment can be most effectively employed when the PArg is higher than nonamer, or in other words, in formula (I), p should be greater than about 20. For example, the PArg can have a weight-average molecular weight of about 5,000, corresponding to a "p" value of about 29. Under the influence of the electronic beam, the peptide bonds of PArg undergo cleavage, causing de-polymerization of PArg. Consequently, the population of the peptide (e.g., R7 or R9) in the stent coating increases. The length of the electronic beam treatment can be about 1 second. The standard equipment used for sterilization of the stents can be used, with the electronic beam having energy of about 2.5 MRad (25 kilograys).

Alternatively, instead of treatment with the electronic beam, the stent can be treated by autoclaving. High pressure and temperature in the autoclave will also cause de-polymerization of PArg leading to the enrichment of the stent coating with the sub-population of R7 or R9. The conditions of autoclaving will be selected by those having ordinary skill in the art.

In accordance with yet another embodiment, the coated stent can be sterilized at a high temperature, for example, above about 100° C. During sterilization, PArg contained in the outermost layer of the stent coating can be exposed to ethylene oxide.

Under conditions of high temperature, the proton at the nitrogen atom of the peptide bond —NH—CO— of PArg will be activated and will attack the oxyran ring of ethylene oxide causing the ring to open forming an ethylene glycol (—CH$_2$—CH$_2$—O—) moiety. As a result poly(ethylene glycol) (PEG) can be chemically bonded to the coating's surface. The path of the reaction can be shown as reaction (II):

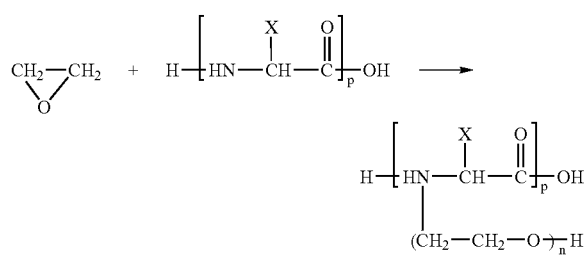

The high temperature treatment in the presence of ethylene glycol thus makes it possible to sterilize the stent and to simultaneously conjugate PEG, a biologically active substance, to the stent coating.

B. Incorporating PArg into Stent Coatings Using Hydrogels

PArg can be incorporated in the stent coating by using hydrogel technology. For example, a hydrogel can be prepared by mixing R7 and poly(glutamic acid) (PGlA). A R7:PGlA ratio can be between about 1:1 and 5:1. Instead of PGlA, other highly carboxylated hydrocarbons can be used in the alternative, for instance, polyalginate, sulfonated dextran, or mixtures thereof. A portion of PGlA or its alternatives can be replaced with other polycationic or polyanionic compounds. Examples of such polycationic or polyanionic compounds include PArg, polylysine, poly(dimethylaminoethyl methacrylate) (PDMAEM), poly(acrylic acid), and polysaccharides.

The hydrogel containing R7 can be mixed with the polymer solution forming the drug-polymer layer or the optional finishing coat layer. The hydrogel can be used to cause endothelialization. Those having ordinary skills in the art may also choose to use the hydrogel in applications not involving stent coatings. Examples of such applications include using the hydrogel in tissue sealants, with biological adhesives designed to accelerate healing, and with biocompatible viscosifiers such as hyaluronic acid or carboxymethyl cellulose.

C. Incorporating PArg into Stent Coatings Using Micro- or Nanoparticles

PArg can be incorporated in the stent coating by being first incorporated into particles of micron to sub-micron size (i.e., micro- or nanoparticles). For example, the particles can have diameter between about 0.5 and 4.0 µm. The particles comprise a sphere-type outer shell made of an encapsulating polymer and an inside space filled with PArg. The particles can be made by an emulsion method according to techniques known to those having ordinary skill in the art. Examples of suitable encapsulating polymers having varying rates of hydrolysis include poly(glycolic acid) (PGA), poly(D-lactic acid) (PDLA), poly(L-lactic acid) (PLLA), poly(butylene terephthalate-co-ethylene glycol), PBT-PEG, and mixtures thereof.

The micro- or nanoparticles containing R7 can be suspended in the polymer solution forming the drug-polymer layer and/or the finishing coat layer and applied onto the stent. The peptide particles-to-polymer ratio can be within a range of between about 1:5 and 1:10. When the stent is in contact with body fluids, the polymer forming the outer shell of the particles will hydrolyze and degrade thus releasing the peptide, such as the R7.

The polycationic peptides can be introduced alone or blended with other active agent(s). Generally speaking, the active agent can include any substance capable of exerting a therapeutic or prophylactic effect in the practice of the present invention. Examples of agents include antiproliferative substances such as actinomycin D, or derivatives and analogs thereof. Synonyms of actinomycin D include dactinomycin, actinomycin IV, actinomycin II, actinomycin X$_1$, and actinomycin C$_1$. The active agent can also fall under the genus of antineoplastic, anti-inflammatory, antiplatelet, anticoagulant, antifibrin, antithrombin, antimitotic, antibiotic, antiallergic and antioxidant substances. Examples of such antineoplastics and/or antimitotics include paclitaxel, docetaxel, methotrexate, azathioprine, vincristine, vinblastine, fluorouracil, doxorubicin hydrochloride, and mitomycin. Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin. Examples of such cytostatic or antiproliferative agents include angiopeptin, angiotensin converting enzyme inhibitors such as captopril, cilazapril or lisinopril, calcium channel blockers (such as nifedipine), colchicine, fibroblast growth factor (FGF) antagonists, fish oil (ω-3-fatty acid), histamine antagonists, lovastatin (an inhibitor of HMG-CoA reductase, a cholesterol lowering drug), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, genetically engineered epithelial cells, rapamycin, derivatives and analogs of rapamycin, estradiol, clobetasol, and dexamethasone. Functional derivatives or structural analogs of the aforementioned drugs can also be used, such as any suitable derivative of rapamycin.

PArg can be synthesized as a dendritic (branched to a large degree) polymer which can fully envelop and thus host the active substance, more particularly cationic agents, leading to synergistic effects. Examples of the biologically active substances suitable of being hosted by PArg in the dendritic form include silver cation and sulfonyl amide.

The coatings and methods of the present invention have been described with reference to a stent, such as a balloon expandable or self-expandable stent. The use of the coating is not limited to stents, however, and the coating can also be used with a variety of other medical devices. Examples of implantable medical devices that can be used in conjunction with the embodiments of this invention include stent-grafts, grafts (e.g., aortic grafts), artificial heart valves, cerebrospinal fluid shunts, pacemaker electrodes, axius coronary shunts and endocardial leads (e.g., FINELINE and ENDOTAK, available from Guidant Corporation). The underlying structure of the device can be of virtually any design. The device can be made of a metallic material or an alloy such as, but not limited to, cobalt-chromium alloys (e.g., ELGILOY), stainless steel (316L), "MP35N," "MP20N," ELASTINITE, Nitinol, tantalum, tantalum-based alloys, nickel-titanium alloy, platinum, platinum-based alloys such as, e.g., platinum-iridium alloy, iridium, gold, magnesium, titanium, titanium-based alloys, zirconium-based alloys, or combinations thereof. Devices made from bioabsorbable or biostable polymers can also be used with the embodiments of the present invention.

"MP35N" and "MP20N" are trade names for alloys of cobalt, nickel, chromium and molybdenum available from Standard Press Steel Co. of Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

Embodiments of the present invention can be further illustrated by the following set forth examples.

EXAMPLE 1

A first composition can be prepared by mixing the following components:

(a) between about 1.0 mass % and about 15 mass %, for example, about 2.0 mass % of EVAL; and (b) the balance, DMAC solvent.

The first composition can be applied onto the surface of a bare 13 mm TETRA stent (available from Guidant Corporation) by spraying and dried to form a primer layer. A spray coater can be used, having a 0.014 fan nozzle maintained at about 60° C. with a feed pressure of about 0.2 atm (about 3 psi) and an atomization pressure of about 1.3 atm (about 20 psi). About 70 μg of the wet coating can be applied. The primer can be baked at about 140° C. for about 2 hours, yielding a dry primer layer.

A second composition can be prepared by mixing the following components:

(c) between about 1.0 mass % and about 15 mass %, for example, about 1.7 mass % of EVAL;

(d) between about 0.05 mass % and about 2.0 mass %, for example, about 0.7 mass % of R7; and (e) the balance, a solvent mixture, comprising i-propanol (IPA), distilled water and DMAC in a ratio IPA:$H_2O$:DMAC of about 1:4:33.

The second composition can be applied onto the dried primer layer to form a first sub-layer of the drug-polymer layer, using the same spraying technique and equipment used for applying the primer layer. About 200 μg of the wet coating can be applied, followed by drying, e.g., by baking as described above.

A third composition, a suspension of R7, can be prepared by mixing the following components:

(f) between about 1.0 mass % and about 15 mass %, for example, about 1.6 mass % of EVAL;

(g) between about 0.05 mass % and about 2.0 mass %, for example, about 0.3 mass % of R7; and (h) the balance, a solvent mixture, comprising i-propanol (IPA), distilled water and DMAC in a ratio IPA:$H_2O$:DMAC of between about 3:1:12 and 6:1:25.

The suspension composition can be applied onto the dried first sub-layer of the drug-polymer layer, to complete forming the drug-polymer layer, using the same spraying technique and equipment used for applying the primer layer and the first sub-layer of the drug-polymer layer. About 200 μg of the suspension can be applied, followed by drying, e.g., by baking as described above.

A fourth composition can be prepared by mixing the following components:

(i) between about 1.0 mass % and about 15 mass %, for example, about 2.0 mass % of PBMA; and (j) the balance, a mixture of solvents, xylene, FLUX REMOVER AMS, and acetone in a ratio of about 25:19:5 by mass.

The fourth composition can be applied onto the dried drug-polymer layer, to form a topcoat layer, using the same spraying technique and equipment. About 100 μg of the wet coating can be applied, followed by drying, e.g., by baking as described above.

A fifth composition can be prepared by mixing the following components:

(k) between about 1.0 mass % and about 15 mass %, for example, about 2.0 mass % of PBMA; and (l) between about 0.05 mass % and about 2.0 mass %, for example, about 0.7 mass % of R7; and (m) the balance, a mixture of solvents, xylene, FLUX REMOVER AMS, and acetone in a ratio of about 25:19:5 by mass.

The fifth composition can be applied onto the dried topcoat layer, to form a finishing coat layer, using the same spraying technique and equipment used for applying the primer, the drug-polymer, and the topcoat layers. About 100 μg of the wet coating can be applied, followed by drying, e.g., by baking as described above.

EXAMPLE 2

A coating comprising a primer layer and a drug-polymer layer can be applied onto a stent, as described in steps (a) through (h) of Example 1. The stent can be placed in a humidifying chamber, at the temperature of about 50° C. and a relative humidity of about 100%, for about 24 hours. A topcoat composition can be prepared by mixing the following components:

(a) between about 1.0 mass % and about 15 mass %, for example, about 2.0 mass % of PBMA; and (b) the balance, a mixture of solvents, xylene, FLUX REMOVER AMS, and acetone in a ratio of about 25:19:5 by mass.

The stent can be removed from the humidifying chamber and dried. The topcoat composition can then be applied onto the drug-polymer layer, to form a topcoat layer, using the same spraying technique and equipment as described in Example 1. About 100 μg of the wet coating can be applied, followed by drying, e.g., by baking as described above.

EXAMPLE 3

A stent coating can be made as described in Example 1, except instead of R7, poly(L-arginine) having weight-average molecular weight of about 5,000 is used. For this kind of PArg, p=29. The coated stent can be then subjected to an electronic beam having an energy of about 2.5 MRad for about 1 second.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for fabricating a coating for an implantable medical device, comprising:
    (a) forming a coating on the device, the coating including a polycationic peptide; and
    (b) treating the coating with a stimulus that cleaves peptide bonds for enriching a region close to the outer surface of the coating with the polycationic peptide.

2. The method of claim 1, wherein the implantable medical device is a stent.

3. The method of claim 1, wherein the polycationic peptide includes poly(L-arginine), poly(D-arginine), poly (D,L-arginine), poly(L-lysine), poly(D-lysine), poly(δ-guanidino-α-aminobutyric acid), and a mixture of poly(L-arginine) and poly(D-arginine).

4. The method of claim 1, wherein the treating of the coating includes subjecting the device to a humid environment at a selected temperature.

5. The method of claim 4, wherein the temperature is about 50° C. and the humidity is about 100%.

6. The method of claim 1, wherein the treating includes subjecting the device to an electronic beam or to autoclaving.

7. The method of claim 6, wherein the electronic beam has energy of about 2.5 MRad.

8. A coating for an implantable medical device, the coating comprising two regions, a first region including a polycationic peptide and a second region free from the polycationic peptide, wherein the polycationic peptide is encapsulated in particles in the coating.

9. The coating of claim 8, wherein the region free from the polycationic peptide is positioned on the surface of the device and beneath the region including the polycationic peptide.

10. The coating of claim 8, wherein the particles are fabricated of a substance selected from a group consisting of poly(glycolic acid), poly(D-lactic acid), poly(L-lactic acid), poly(butylene terephtalate-co-ethylene glycol) and mixtures thereof.

11. A method of modifying a coating for an implantable medical device, the coating including a polycationic peptide, comprising exposing the coating to ethylene oxide at a selected temperature and conjugating poly(ethylene glycol) to the coating.

12. A method of fabricating a coating for a medical device, comprising forming a coating on the device, the coating including a polycationic peptide, and causing some of the peptide bonds in the polycationic peptide to be cleaved, whereby the population of free peptides in the coating is increased.

13. The method of claim 11, wherein the polycationic peptide includes poly(L-arginine), poly(D-arginine), poly (D,L-arginine), poly(L-lysine), poly(D-lysine), poly(δ-guanidino-α-aminobutyric acid), and a mixture of poly(L-arginine) and poly(D-arginine).

14. The method of claim 11, wherein the device is a stent.

15. The method of claim 12, wherein the polycationic peptide includes poly(L-arginine), poly(D-arginine), poly (D,L-arginine), poly(L-lysine), poly(D-lysine), poly(δ-guanidino-α-aminobutyric acid), and a mixture of poly(L-arginine) and poly(D-arginine).

16. The method of claim 12, wherein the device is a stent.

17. A method of fabricating a coated stent, comprising forming a coating comprising two regions on the stent wherein the coating includes a first region containing a peptide and a second region free from the peptide wherein the peptide is encapsulated in particles in the coating.

18. A coating for a medical device comprising a peptide that has been cleaved such that the population of the peptide is greatest at the outmost region of the coating.

19. The coating of claim 8, wherein the implantable medical device is a stent.

20. The coating of claim 8, wherein the polycationic peptide includes poly(L-arginine), poly(D-arginine), poly (D,L-arginine), poly(L-lysine), poly(D-lysine), poly(δ-guanidino-α-aminobutyric acid), and a mixture of poly(L-arginine) and poly(D-arginine).

21. The method of claim 17, wherein the implantable medical device is a stent.

22. The method of claim 17, wherein the polycationic peptide includes poly(L-arginine), poly(D-arginine), poly (D,L-arginine), poly(L-lysine), poly(D-lysine), poly(δ-guanidino-α-aminobutyric acid), and a mixture of poly(L-arginine) and poly(D-arginine).

* * * * *